(12) United States Patent
Plambech et al.

(10) Patent No.: US 11,458,251 B2
(45) Date of Patent: Oct. 4, 2022

(54) DRUG DELIVERY DEVICE WITH SLIM DRIVE MECHANISM

(71) Applicant: Novo Nordisk A/S, Bagsvaerd (DK)

(72) Inventors: Christian Plambech, Soeborg (DK); Jesper Peter Windum, Hilleroed (DK); Lars Peter Klitmose, Gentofte (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 15/766,581

(22) PCT Filed: Oct. 7, 2016

(86) PCT No.: PCT/EP2016/073999
§ 371 (c)(1),
(2) Date: Apr. 6, 2018

(87) PCT Pub. No.: WO2017/060426
PCT Pub. Date: Apr. 13, 2017

(65) Prior Publication Data
US 2018/0289895 A1  Oct. 11, 2018

(30) Foreign Application Priority Data
Oct. 9, 2015 (EP) .................................... 15189050

(51) Int. Cl.
*A61M 5/20* (2006.01)
*A61M 5/315* (2006.01)
*A61M 5/24* (2006.01)

(52) U.S. Cl.
CPC .......... *A61M 5/20* (2013.01); *A61M 5/31553* (2013.01); *A61M 5/31583* (2013.01);
(Continued)

(58) Field of Classification Search
CPC .. A61M 5/20; A61M 5/2033; A61M 5/31533; A61M 5/31583; A61M 5/31585;
(Continued)

(56) References Cited

U.S. PATENT DOCUMENTS 8,048,037 B2  11/2011  Kohlbrenner et al.
8,398,593 B2   3/2013  Eich et al.
(Continued)

FOREIGN PATENT DOCUMENTS

EP        2692376 A1   2/2014
JP     2015517856 A   6/2015
(Continued)

*Primary Examiner* — Tiffany Legette
*Assistant Examiner* — Antarius S Daniel
(74) *Attorney, Agent, or Firm* — Wesley Nicolas

(57) ABSTRACT

A drug delivery device comprises a housing (201) and an expelling assembly with a piston rod (220), a drive tube (260) with an outer surface and a scale drum (270) arranged between the drive tube and the housing, the scale drum being coupled to the housing and the drive tube outer surface. The device further comprises a drive spring (255) arranged between the housing and the drive tube, and setting means (280) allowing a user to simultaneously set a dose amount to be expelled and strain the drive spring correspondingly by rotation of the drive tube. The scale drum is coupled to the drive tube via a spline connection, wherein the drive spring is arranged proximally of the spline connection when the spline connection is in its proximal-most position.

12 Claims, 11 Drawing Sheets

(52) U.S. Cl.
CPC ..... *A61M 5/31535* (2013.01); *A61M 5/31541* (2013.01); *A61M 5/31543* (2013.01); *A61M 2005/2411* (2013.01)

(58) Field of Classification Search
CPC .......... A61M 5/31535; A61M 5/31536; A61M 5/31541; A61M 5/31543; A61M 5/31528; A61M 5/3155; A61M 5/31551; A61M 5/31553; A61M 2005/2093; A61M 2005/3125; A61M 2005/2411
See application file for complete search history.

(56) References Cited

U.S. PATENT DOCUMENTS

| | | | |
|---|---|---|---|
| 10,195,359 | B2 | 2/2019 | Pedersen et al. |
| 2006/0004297 | A1 | 1/2006 | Orr et al. |
| 2006/0153693 | A1 | 7/2006 | Fiechter et al. |
| 2008/0243087 | A1 | 10/2008 | Enggaard et al. |
| 2008/0306445 | A1* | 12/2008 | Burren ............... A61M 5/24 604/136 |
| 2009/0247951 | A1* | 10/2009 | Kohlbrenner ........... A61M 5/20 604/134 |
| 2009/0254044 | A1 | 10/2009 | Kohlbrenner et al. |
| 2011/0054412 | A1* | 3/2011 | Eich ................... A61M 5/20 604/207 |
| 2011/0092905 | A1* | 4/2011 | Cowe .................. A61M 5/20 604/135 |
| 2013/0204193 | A1 | 8/2013 | Holmqvist |
| 2014/0088515 | A1* | 3/2014 | Karlsson ............... A61M 5/20 604/209 |
| 2015/0196716 | A1 | 7/2015 | Streit et al. |

FOREIGN PATENT DOCUMENTS

| | | |
|---|---|---|
| WO | 02/053214 A1 | 7/2002 |
| WO | 2004078239 A1 | 9/2004 |
| WO | 2006045526 A1 | 5/2006 |
| WO | 2007017053 A1 | 2/2007 |
| WO | 2009105908 A1 | 9/2009 |
| WO | 2014001319 A1 | 1/2014 |
| WO | 2014060369 A1 | 4/2014 |
| WO | 2014170267 A1 | 10/2014 |
| WO | 2015055642 A1 | 4/2015 |
| WO | 2015075134 A1 | 5/2015 |

* cited by examiner

DRUG DELIVERY DEVICE WITH SLIM DRIVE MECHANISM

CROSS-REFERENCE TO RELATED APPLICATIONS

This application is a 35 U.S.C. § 371 National Stage application of International Application PCT/EP2016/073999 (published as WO 2017/060426), filed Oct. 7, 2016, which claims priority to European Patent Application 15189050.6, filed Oct. 9, 2015, the contents thereof which are incorporated by reference in their entirety.

The present invention generally relates to drug delivery devices adapted to expel a user settable dose of drug from a cartridge. In a specific aspect the invention relates to a spring-driven device.

BACKGROUND OF THE INVENTION

In the disclosure of the present invention reference is mostly made to the treatment of diabetes, however, this is only an exemplary use of the present invention.

A general type of drug delivery devices suitable for delivery of a user set amount of drug comprises a spring which is strained during dose setting, the stored energy subsequently being used to expel the set dose of drug from a cartridge arranged in the device. The user usually strains a spring by rotating a rotatable dose setting member, the force thereby applied by the user being stored in the spring for later release. This type of drug delivery device may be provided either in the form of a pre-filled disposable device or in the form of a durable device adapted to be loaded with a drug cartridge by the user.

Examples of known "wind-up" or "auto-pen" drug delivery devices having a pen-formed configuration and comprising a torsion spring are disclosed in e.g. WO 2006/045526 in which the device utilizes a helical spring and WO 2009/105908 in which the device utilizes a spiral clock-type spring. These pens also allow the user to decrease the set dose prior to dosing by rotating the dose setting member in an opposite rotational direction. Further devices of the spring-driven type are disclosed in EP 2 692 376, WO 2007/017053, WO 2014/001319, US 2006/0153693 and US 2011/0054412.

As an alternative to the wind-up type of automatic drug delivery devices, devices have been proposed which are provided with a pre-strained spring in which sufficient energy is stored for expelling the entire dispensable amount of drug contained in a cartridge, e.g. 3 ml. The dose setting means will typically be similar to the above-described dial-up/dial-down arrangements allowing a user to set and adjust a dose to be expelled.

However, as more features are added to a pen-formed drug delivery device more components will normally be required which again in most cases will add to the dimensions and bulk of the device, especially the diameter, e.g. as exemplified by comparing the relatively slim manually driven FlexPen® with the somewhat less slim FlexTouch® auto-pen, both from Novo Nordisk.

Having regard to the above, it is an object of the present invention to provide a drug delivery device of the automatic spring-driven type which is compact, simple and reliable and allows for cost-effective manufacturing.

DISCLOSURE OF THE INVENTION

In the disclosure of the present invention, embodiments and aspects will be described which will address one or more of the above objects or which will address objects apparent from the below disclosure as well as from the description of exemplary embodiments.

The present invention is based on the concept of re-arranging the components of a spring-driven drug delivery device in such a way that structures which hitherto have been arranged concentrically are now arranged axially apart instead.

Thus, in a first aspect of the invention a drug delivery device is provided comprising or adapted to receive a drug-filled cartridge, the drug delivery device comprising a housing and an expelling assembly. The expelling assembly comprises a piston rod adapted to engage and axially displace a piston in a loaded cartridge in a distal direction to thereby expel a dose of drug from the cartridge, the piston rod having a proximal-most position, a drive tube at least partially accommodating the piston rod, and a drive member arranged in engagement with the piston rod and adapted to rotate the piston rod. The expelling assembly further comprises a drive spring arranged in engagement with the housing and the drive tube, setting means allowing a user to simultaneously set a dose amount to be expelled and strain the drive spring correspondingly by rotation of the drive tube, a scale drum helically coupled to the housing as well as axially moveable but non-rotatably coupled to the drive tube, the scale drum thereby being moved helically as the drive tube is rotated, coupling means actuatable between a dose setting state in which the drive tube can be rotated to a set position, and an expelling state in which the drive tube driven by the drive spring can rotate the drive member, and release means actuatable between a dose setting state and an expelling state to thereby actuate the coupling means. The drive spring can be released to rotate the drive tube and thereby the drive member to thereby rotate and move the piston rod in the distal direction. The scale drum is coupled to the drive tube via a spline connection, the spline connection during dose setting having a proximal-most position corresponding to a proximal-most position of the scale drum, wherein the drive spring is arranged proximally of the spline connection when the spline connection is in its proximal-most position.

In the present context the "position" of the spline connection corresponds to the proximal-most point of engagement between a groove and a ridge structure. Depending on the arrangement of the scale drum the proximal-most position of the scale drum may correspond to the initial position or correspond to a set maximum dose. When the piston rod is rotated by the driver, axial movement may be generated e.g. by a threaded connection between the piston rod and a housing "nut" portion or by a threaded connection between the piston rod and the driver.

By the above arrangement a more compact drug delivery device can be provided, allowing portions of the device to be designed with fewer "layers" which again allows for a slimmer design, this in contrast to the "multi-layer" designs known from the prior art. For example, in prior art devices the drive tube is at its distal end provided with a proximally extending circumferential skirt portion. In such a design the drive spring is arranged between the skirt and the main drive tube with the scale drum in splined engagement with the skirt portion outer surface. In contrast, when the scale drum/drive tube spline connection and the drive spring are axially offset, a more compact device can be achieved.

The drive tube in accordance with the invention may be in the form of an assembly in which the drive tube for e.g. molding or assembling reasons is comprised of e.g. two tubular members fully or partly overlapping each other axially. For such a design the scale drum may engage the drive tube corresponding to e.g. a non-overlapping or overlapping portion.

The spline connection may comprise a proximal-most ridge structure in sliding engagement with a corresponding groove, the groove being formed in the scale drum inner surface and the proximal-most ridge structure being formed on the drive tube outer surface, whereby the proximal-most ridge structure, and thereby the spline connection, has an axial position which does not move during dose setting. Indeed, if the drive tube is axially displaced during actuation the spline position will move therewith. Depending on the drive spring arrangement the drive spring may also move during actuation.

Alternatively, the spline connection comprises a proximal-most ridge structure in sliding engagement with a corresponding groove, the groove being formed in the drive tube outer surface and the proximal-most ridge structure being formed on the scale drum inner surface, whereby the proximal-most ridge structure, and thereby the spline connection, has an axial position which moves during dose setting. Typically all ridge structures in a given spline connection are located at the same axial position.

In a specific embodiment the drug delivery device comprises a housing and an expelling assembly, the latter comprising a piston rod arranged to engage and axially displace a piston in a loaded cartridge in a distal direction to thereby expel a dose of drug from the cartridge, a drive tube at least partially accommodating the piston rod, a drive member arranged in engagement with the piston rod and adapted to rotate the piston rod, and a drive spring arranged in engagement with the housing and the drive tube. The expelling assembly further comprises setting means allowing a user to simultaneously set a dose amount to be expelled and strain the drive spring correspondingly by rotation of the drive tube, a scale drum helically coupled to the housing as well as axially moveable but non-rotatably coupled to the drive tube, the scale drum thereby being moved helically as the drive tube is rotated. The expelling assembly further comprises coupling means actuatable between a dose setting state in which the drive tube can be rotated to a set position, and an expelling state in which the drive tube driven by the drive spring can rotate the drive member, and release means actuatable between a dose setting state and an expelling state to thereby actuate the coupling means.

The drive spring can be released to rotate the drive tube and thereby the drive member to thereby rotate and move the piston rod in the distal direction. The scale drum is coupled to the drive tube via a spline connection, the spline connection comprising one or more ridge structures formed on the drive tube outer surface and being in sliding engagement with one or more corresponding grooves formed in the scale drum inner surface. The drive spring is arranged proximally of the one or more ridge structures.

In a further specific embodiment the drug delivery device comprises a housing, a piston rod, a drive member adapted to rotate the piston rod, a scale drum helically coupled to the housing and comprising one or more axially oriented grooves formed in the scale drum inner surface, a drive tube comprising one or more ridge structures formed on the drive tube outer surface and being in sliding engagement with the one or more corresponding grooves formed in the scale drum inner surface, a drive spring arranged in engagement with the housing and the drive tube, setting means allowing a user to simultaneously set a dose amount to be expelled and strain the drive spring correspondingly by rotation of the drive tube, coupling means actuatable between a dose setting state in which the drive tube can be rotated to a set position, and an expelling state in which the drive tube driven by the drive spring can rotate the drive member, and release means actuatable between a dose setting state and an expelling state to thereby actuate the coupling means. In such an arrangement the drive spring is arranged proximally of the one or more ridge structures.

In a yet further specific embodiment the drug delivery device comprises a housing, a piston rod, a drive member adapted to rotate the piston rod, a scale drum helically coupled to the housing and comprising one or more ridge structures formed in the scale drum inner surface, a drive tube comprising one or more axially oriented grooves formed on the drive tube outer surface and being in sliding engagement with the one or more corresponding ridge structures formed in the scale drum inner surface, a drive spring arranged in engagement with the housing and the drive tube, setting means allowing a user to simultaneously set a dose amount to be expelled and strain the drive spring correspondingly by rotation of the drive tube, coupling means actuatable between a dose setting state in which the drive tube can be rotated to a set position, and an expelling state in which the drive tube driven by the drive spring can rotate the drive member, and release means actuatable between a dose setting state and an expelling state to thereby actuate the coupling means, wherein the drive spring is arranged proximally of the one or more ridge structures in their proximal-most position.

In an exemplary embodiment the drive spring is a helical spring, the drive spring with the scale drum in its proximal-most position being arranged at least partially between the scale drum and the drive tube and thereby at least partially overlapping. Alternatively, the drive spring is a non-helical clock spring, the drive spring with the scale drum in its proximal-most position being arranged either proximally of the scale drum or at least partly axially overlapping.

The release means may be in the form of a release member axially moveable between a proximal dose setting position and an actuated distal dose expelling position.

In an exemplary embodiment the setting means comprises a rotatable dose setting member and the coupling means comprises a first coupling arrangement actuatable between a dose setting state in which the setting member is rotationally locked to the drive tube and in which the drive tube can be held in a set position against the biasing force of the strained drive spring, and an expelling state in which the drive tube is rotationally de-coupled from the dose setting member and is allowed to be rotated by the drive spring, and a second coupling arrangement actuatable between a dose setting state in which the drive tube can rotate relative to the drive member and an expelling state in which the drive tube is rotationally locked to the drive member. In such an arrangement the release means, when actuated, actuates the first coupling arrangement from the dose setting state to the expelling state, and actuates the second coupling arrangement from the dose setting state to the expelling state. The first and/or second coupling arrangement may be of the spline-type in which a pair of cooperating structures has a coupled state in which a splined connection prevents relative rotation there between, and a de-coupled state in which the splines are moved axially out of engagement with each other this allowing relative rotation there between.

The dose setting member may be coupled to and move axially with the release member. For example, the dose setting member and the release member may be formed by a combined dose setting and release member or assembly.

In an exemplary embodiment the coupling means comprises a ratchet mechanism allowing the drive tube to be held in a set position against the biasing force of the strained drive spring. The ratchet mechanism may be in the form of a releasable one-way ratchet mechanism allowing a set dose to be reduced. The ratchet mechanism may be associated with either the first or the second coupling arrangement, e.g. arranged corresponding to the proximal end of the device or corresponding to the distal end of the drive tube.

In an exemplary embodiment the ratchet mechanism comprises a first ratchet part comprising a plurality of ratchet teeth, the first ratchet part being non-rotationally coupled to the housing during dose setting, a second ratchet part comprising a plurality of ratchet teeth adapted to rotationally engage the ratchet teeth on the first ratchet part, the second ratchet part being non-rotationally coupled to the drive member during dose setting, the first and second ratchet parts being axially moveable relative to each other during dose setting, and bias means for axially biasing the first and second ratchet parts into engagement with each other. The ratchet mechanism further comprises control means adapted to rotate the second ratchet part in the first direction to thereby set a dose when the dose setting member is rotated in the first direction, and move the first and second ratchet parts axially out of engagement with each other when the dose setting member is rotated in the second direction.

The control means may comprise a combined drive-release ratchet having a plurality of ratchet drive surfaces and a plurality of ratchet release surfaces inclined relative to a rotational reference plane, and a control ratchet comprising a plurality of control drive surfaces and a plurality of control release surfaces inclined relative to the rotational reference plane. In such an arrangement the control drive surfaces are cooperating with the ratchet drive surfaces to rotate the second ratchet part in the first direction when the dose setting member is rotated in the first direction, and the control release surfaces are slidingly cooperating with the ratchet release surfaces to axially move the first and second ratchet parts axially out of engagement with each other when the dose setting member is rotated in the second direction, whereby, when the first and second ratchet parts have been axially dis-engaged, the drive spring will rotate the second ratchet part in the second direction to thereby reduce the set dose, the bias means moving the first and second ratchet parts axially into engagement with each other again, this resulting in the set dose being reduced corresponding to one tooth of the ratchet mechanism.

In an exemplary embodiment the drive tube may comprise a proximal portion and a distal portion, the proximal portion having a smaller diameter than the distal portion, this providing space for the drive spring to be arranged correspondingly to the drive tube proximal portion.

In a further exemplary embodiment the expelling assembly comprises an end-of-content member arranged in the circumferential space between the piston rod and the drive tube corresponding to the distal portion, wherein the end-of-content member is axially moveable between a distal position and a proximal position relative to the piston rod. The end-of-content member may be in threaded engagement with the piston rod and splined engagement with the drive tube. Alternatively, the drive member may be provided with a proximally extending threaded portion, wherein the end-of-content member is in threaded engagement therewith and in splined engagement with the drive tube.

For the above-described embodiments, the drive spring may be in the form of a non-helical clock spring which may be pre-strained.

In an exemplary embodiment the drug delivery device comprises a cartridge holder adapted to receive and hold a cartridge in a mounted state, the cartridge holder being actuatable between (i) a receiving state in which a cartridge can be received, and (ii) a holding state in which a received cartridge is held in an operational mounted position. The device further comprises a resetting coupling having an actuated state in which an extended piston rod can be moved proximally, wherein the resetting coupling is actuated from the locked state to the un-locked state when the cartridge holder is actuated from the holding state to the receiving state. The cartridge holder may be front-loaded and adapted to receive a cartridge in a proximal direction.

In a further aspect of the invention a drug delivery device is provided comprising or adapted to receive a drug-filled cartridge, the drug delivery device comprising a housing and an expelling assembly. The expelling assembly comprises a piston rod adapted to engage and axially displace a piston in a loaded cartridge in a distal direction to thereby expel a dose of drug from the cartridge, a drive tube at least partially accommodating the piston rod, the drive tube having a generally tubular configuration with a tubular wall portion having an outer surface and an inner surface, the inner surface facing at least a portion of the piston rod when the piston rod is in its proximal-most position (i.e. no structures are arranged there between), and a drive member arranged in engagement with the piston rod, the piston rod being axially moveable relatively to the drive member, whereby rotation of the drive member provides that the piston rod is moved axially. The expelling assembly further comprises a drive spring arranged between the housing and the drive tube, setting means allowing a user to simultaneously set a dose amount to be expelled and strain the drive spring correspondingly by rotation of the drive tube, a scale drum arranged at least in part between the housing and the drive tube, the scale drum being helically coupled to the housing as well as axially moveable but non-rotatably coupled to the tubular wall portion outer surface of the drive tube, the scale drum thereby being moved helically as the drive tube is rotated, coupling means actuatable between a dose setting state in which the drive tube can be rotated to a set position, and an expelling state in which the drive tube driven by the drive spring can rotate the drive member, and release means actuatable between a dose setting state and an expelling state to thereby actuate the coupling means. The drive spring can be released to rotate the drive tube and thereby the drive member to thereby move the piston rod in the distal direction to thereby expel a dose of drug from a cartridge.

By this arrangement a more compact drug delivery device can be provided, allowing portions of the device to be designed with fewer "layers" which again allows for a slimmer design, this in contrast to the "multi-layer" designs known from the prior art. For example, in prior art devices the drive tube is at its distal end provided with a proximally extending circumferential skirt portion. In such a design the drive spring is arranged between the skirt and the main drive tube with the scale drum in engagement with the skirt portion outer surface. In contrast, when the scale drum in accordance with the present invention is in engagement with the outer surface of the drive tube a more compact device can be achieved.

This said, the drive tube in accordance with the invention may be in the form of an assembly in which the drive tube for e.g. molding or assembling reasons is comprised of e.g. two tubular members fully or partly overlapping each other axially. For such a design the tubular wall portion of the drive tube in the overlapping portion would have an outer surface formed by the outer tubular member and the inner surface formed by the inner tubular member. The scale drum may engage the drive tube corresponding to e.g. a non-overlapping or overlapping portion.

Such an arrangement may be modified corresponding to the above-described embodiments.

In a yet further aspect of the invention a drug delivery device is provided comprising or adapted to receive a drug-filled cartridge, the drug delivery device comprising a housing and an expelling assembly. The expelling assembly comprises a piston rod adapted to engage and axially displace a piston in a loaded cartridge in a distal direction to thereby expel a dose of drug from the cartridge, a drive tube at least partially accommodating the piston rod, and a drive spring arranged between the housing and the drive tube. The expelling assembly further comprises setting means allowing a user to simultaneously set a dose amount to be expelled and strain the drive spring correspondingly by rotation of the drive tube, a scale drum arranged at least in part between the drive tube and the housing, the scale drum being helically coupled to the housing as well as axially moveable but non-rotatably coupled to the drive tube, the scale drum thereby being moved helically as the drive tube is rotated, and release means actuatable from a dose setting state to an expelling state. The piston rod has a proximal-most position in which for at least a portion of its length no structures are arranged between the piston rod and the drive tube inner surface, the drive tube is rotationally de-coupled from the piston rod when the release means is in the dose setting state and rotationally coupled to the piston rod when the release means is in the expelling state, and the drive spring is released when the release means is actuated, thereby rotating the drive tube, the rotating drive tube driving the piston rod in the distal direction corresponding to the set dose.

By this arrangement a more compact drug delivery device can be provided, allowing portions of the device to be designed with fewer "layers" which again allows for a slimmer design.

In exemplary embodiments the expelling assembly further comprises a drive member arranged in engagement with the piston rod, the piston rod being axially moveable relatively to the drive member, whereby rotation of the drive member provides that the piston rod is moved axially, wherein the release means comprises first coupling means for holding the drive tube and thereby the drive spring in a set rotational position, and second coupling means for coupling the drive tube into engagement with the drive member, and the second coupling means is arranged at the distal end of the drive tube. In this way further components can be arranged axially apart instead of concentrically.

The second coupling means may comprise a ratchet member coupled to the housing and arranged to rotate uni-directionally, and a coupling member coupled to the ratchet member and the drive member to transfer rotational movement of the ratchet member to the drive member, wherein the drive tube is moved into non-rotational engagement with the ratchet member when the release means is actuated from the dose setting state to the expelling state.

In an exemplary embodiment the coupling member is coupled to the ratchet member by a first spline coupling allowing the two members to move axially relative to each other, and coupled to the drive member by a second spline coupling allowing the two members to move axially relative to each other. The coupling member can be actuated axially from a locked state in which the first and second spline couplings are engaged, to an un-locked state in which at least one of the first and second spline couplings is released (e.g. the first), this allowing the drive member and thereby the piston rod to rotate relative to the ratchet member.

The drug delivery device may further comprise a cartridge holder adapted to receive and hold a cartridge in a mounted state, the cartridge holder being actuatable between a receiving state in which a cartridge can be received, and a holding state in which a received cartridge is held in an operational mounted position, wherein the coupling member is actuated from the locked state to the un-locked state when the cartridge holder is actuated from the holding state to the receiving state.

The cartridge holder may be front-loaded and adapted to receive a cartridge in a proximal direction through a distal opening, the cartridge holder being actuated by e.g. rotation of an actuation member. Alternatively the cartridge holder may be rear-loaded and adapted to receive a cartridge in a distal direction through a proximal opening, the cartridge holder being actuated by being removed from the drug delivery main portion, e.g. by rotation.

In exemplary embodiments of the above-described drug delivery devices the drive tube comprises a proximal portion and a distal portion, the proximal portion has a smaller diameter, the drive spring being arranged corresponding to the drive tube proximal portion.

Further, the expelling assembly may comprise an end-of-content member arranged in the circumferential space between the piston rod and the drive tube corresponding to the distal portion, the end-of-content member being axially moveable between a distal position and a proximal position relative to the piston rod. The end-of-content member may be in threaded engagement with the piston rod and splined engagement with the drive tube. In such an arrangement the drive member may comprise a proximally extending threaded portion, the end-of-content member being in treaded engagement therewith and in splined engagement with the drive tube.

The drive spring may be in the form of a non-helical clock spring which may be pre-strained.

As used herein, the term "insulin" is meant to encompass any drug-containing flowable medicine capable of being passed through a delivery means such as a cannula or hollow needle in a controlled manner, such as a liquid, solution, gel or fine suspension, and which has a blood glucose controlling effect, e.g. human insulin and analogues thereof as well as noninsulins such as GLP-1 and analogues thereof. In the description of exemplary embodiments reference will be made to the use of insulin.

BRIEF DESCRIPTION OF THE DRAWINGS

In the following exemplary embodiments of the invention will be further described with reference to the drawings, wherein.

In the figures like structures are mainly identified by like reference numerals.

DESCRIPTION OF EXEMPLARY EMBODIMENTS

Figure 1A:
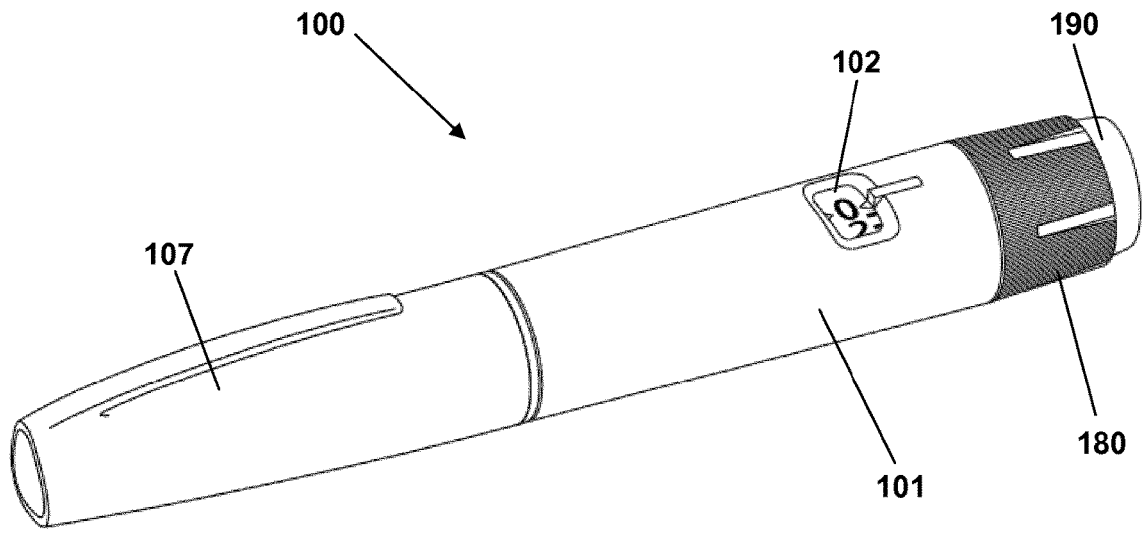
FIGS. 1A and 1B show an embodiment of a drug delivery device.

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member or element is used for a given component it generally indicates that in the described embodiment the component is a unitary component, however, the same member or element may alternatively comprise a number of sub-components just as two or more of the described components could be provided as unitary components, e.g. manufactured as a single injection moulded part. The term "assembly" does not imply that the described components necessarily can be assembled to provide a unitary or functional assembly during a given assembly procedure but is merely used to describe components grouped together as being functionally more closely related.

Before turning to embodiments of the present invention per se, an example of a "generic" resettable dial-up/dial down automatic drug delivery device will be described, such a device providing the basis for the exemplary embodiment of the present invention.

The pen device 100 comprises a cap part 107 and a main part having a proximal body or drive assembly portion with a housing 101 in which a drug expelling mechanism is arranged or integrated, and a distal cartridge holder portion in which a drug-filled transparent cartridge 113 with a distal needle-penetrable septum is arranged and retained in place by a cartridge holder attached to the proximal portion, the cartridge holder having openings allowing a portion of the cartridge to be inspected. Distal coupling means 115 allows a needle assembly to be releasably mounted in fluid communication with the cartridge interior. The cartridge is provided with a piston driven by a piston rod forming part of the expelling mechanism and may for example contain an insulin, GLP-1 or growth hormone formulation. A proximal-most rotatable dose setting member 180 serves to manually set a desired dose of drug shown in display window 102 and which can then be expelled when the button 190 is actuated. Depending on the type of expelling mechanism embodied in the drug delivery device, the expelling mechanism may comprise a torsion spring as in the shown embodiment which is strained during dose setting and then released to drive the piston rod when the release button is actuated. More specifically, during dose setting a drive member to which the spring is connected is rotated to a rotational position corresponding to the set dose, the drive member thereby being in an energized state. A scale drum with dose size numerals is coupled to the drive member such that the size of the currently set dose is shown in the display window, e.g. by means of a threaded connection with the housing. To prevent the drive member from rotating the dose setting mechanism is provided with a holding mechanism, which in the shown embodiment is in the form of a ratchet mechanism. When the user desires to expel the set dose the button is actuated whereby the drive member is brought into engagement with the piston rod drive mechanism and the holding mechanism subsequently released.

Figure 1B:
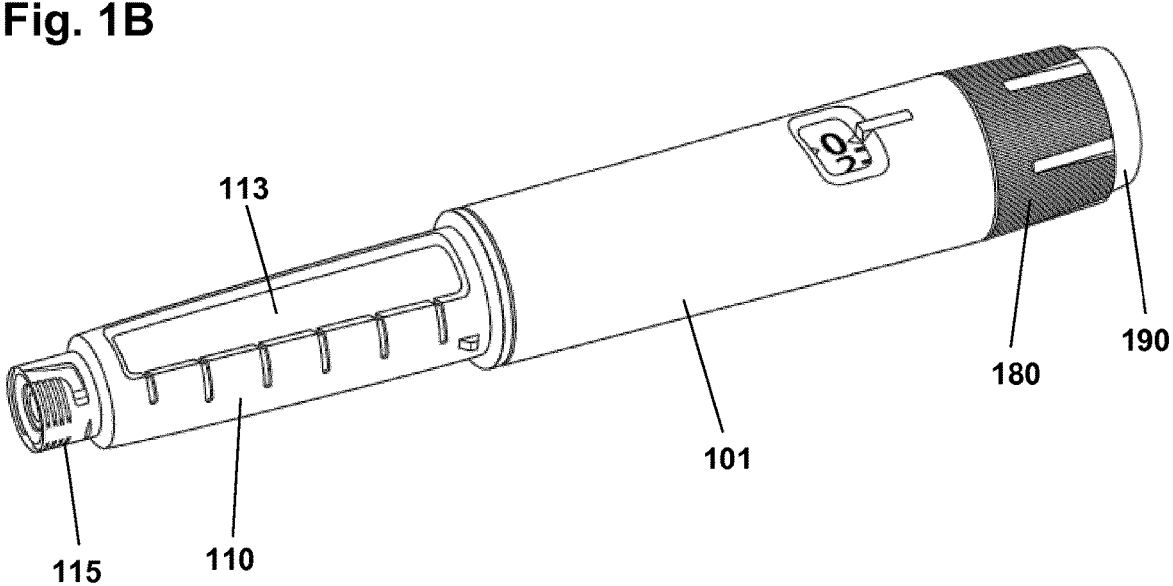

Although FIGS. 1A and 1B show a drug delivery device of the pre-filled type, i.e. it is supplied with a pre-mounted cartridge and is to be discarded when the cartridge has been emptied, in alternative embodiments the drug delivery device may be designed to allow a loaded cartridge to be replaced, e.g. in the form of a "rear-loaded" drug delivery device in which the cartridge holder is adapted to be removed from the device main portion, or alternatively in the form of a "front-loaded" device in which a cartridge is inserted through a distal opening in the cartridge holder which is non-removable attached to the main part of the device.

With reference to FIGS. 2-7 a first exemplary embodiment incorporating aspects of the present invention, a compact resettable dose setting mechanism for a drug delivery device, will be described. The mechanism basically comprises a housing portion 201, a drive tube 260, a torsion drive spring 255 arranged between the housing and the drive tube, a transmission member 240, a dose setting member 280, a release button 290 and a return spring 295.

A detailed description of the working principle of the mechanism will be given below, however, first some of the central components of the dose setting mechanism will be described in detail.

Figure 2:
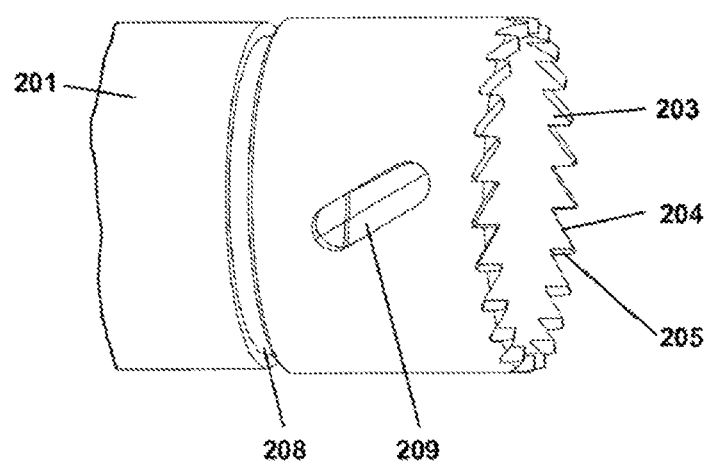
FIG. 2 shows a ratchet part of a first embodiment of a drug delivery device.

Turning to FIG. 2 a proximal portion of a tubular housing member 201 defining a longitudinal axis is shown. The housing member comprises a circumferential proximal edge with a plurality of ratchet teeth structures 203 (here: 24), each tooth having a triangular configuration with an inclined ratchet surface 204 and a stop surface 205 oriented perpendicularly to the housing member cross-sectional plane. The housing further comprises a circumferential groove 208 adapted to engage the dose setting member and arranged between the groove and the proximal end a number of inclined slots 209 (here: three) adapted to engage a spring housing (see below). In this way a first ratchet part coupled non-rotationally to the housing and comprising a plurality of ratchet teeth is formed. As appears, in this embodiment the first ratchet part is formed integrally with the tubular housing member.

Figure 4:
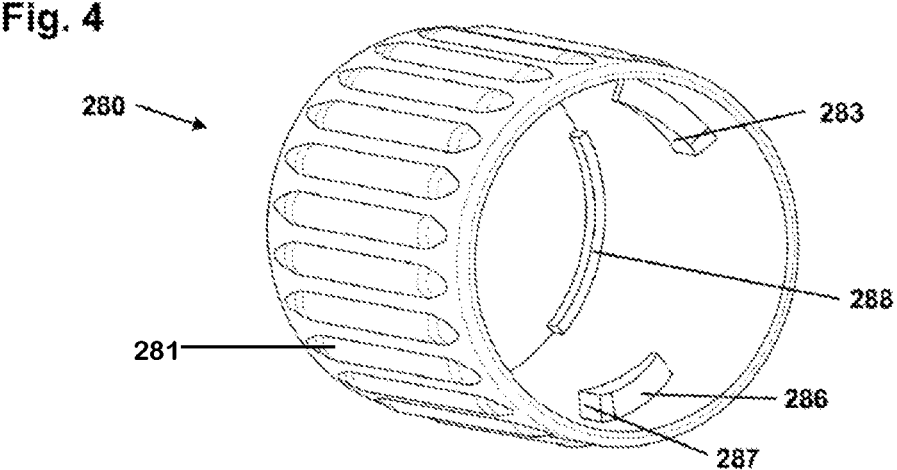
FIG. 4 shows a dose setting member of the first embodiment.

FIG. 4 shows the dose setting member 280 having a generally tubular configuration with an outer cylindrical surface with a plurality of longitudinally arranged ridges 281 providing a grip-ping surface, and an inner cylindrical surface comprising a at the distal end a number of circumferential flange portions 288 adapted to be rotationally arranged in the housing member circumferential groove. The inner surface further comprises a number of triangular "drive-release" og "drive-lift" control ratchet structures 283

(here: three) adapted to engage the transmission member as will be described below, each drive-lift control structure comprising a longitudinally oriented drive surface 287 and an inclined lift surface 286. In the following description the term "drive-lift" will be used.

Figure 3:
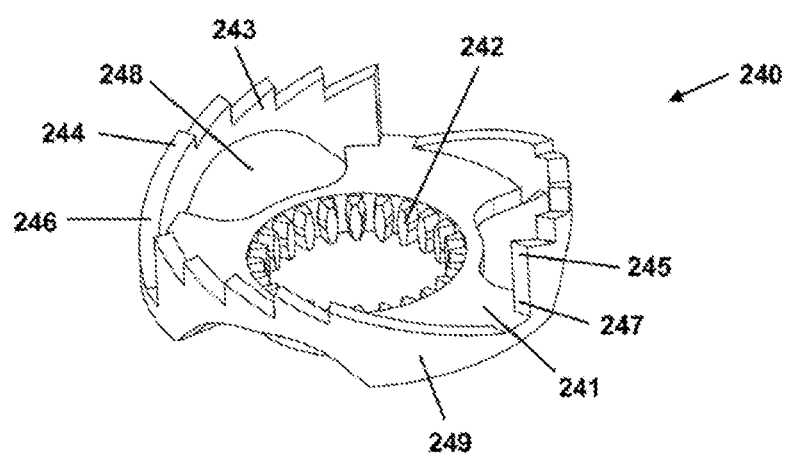
FIG. 3 shows a further ratchet part of the first embodiment.

FIG. 3 shows the transmission member 240 having a ring-shaped body portion 241 with a central opening provided with a plurality of longitudinally arranged splines 242 adapted to slidingly engage corresponding spline grooves on the drive tube. The transmission member further comprises a number of ratchet sections 249 (here: three) between which are formed three drive sections. Each ratchet section comprises a number of ratchet teeth 243 adapted to engage the housing member ratchet teeth 203 to provide a one-way ratchet. In this way a second ratchet part is formed. For a given ratchet section the leading inclined ratchet surface 244 is extended to form a lift surface 246, just as the trailing stop surface 245 is also extend-ed longitudinally to form a drive surface 247. In this way each drive section is defined be-tween an extended ratchet surface and an extended stop surface. Corresponding to each ratchet section an opening 248 is formed in the body portion to allow passage of a release button leg portion (see below).

Figure 5:
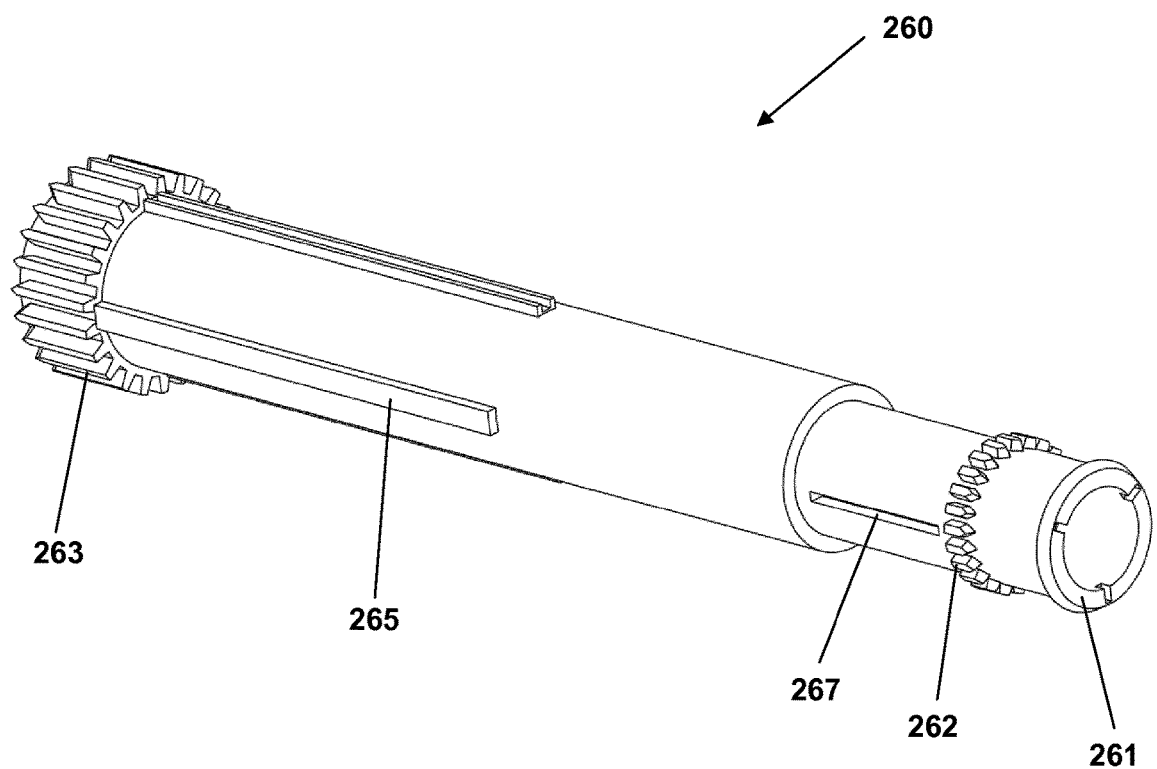
FIG. 5 shows a drive member of the first embodiment.

FIG. 5 shows the drive tube 260 having a proximal-most circumferential flange 261, a proximal array of circumferential splines 262 and a distal array of circumferential splines 263. The flange is adapted to engage release button snap members 291, the proximal splines are adapted to engage the transmission member splines 242 to provide a release coupling, and the distal splines are coupling splines adapted to axially engage the piston driver 230 during actuation to provide a drive coupling. The drive tube further comprises a proximal narrow-diameter portion with an axial slot 267 for attaching the inner end of the drive spring, as well as a distal larger-diameter portion with a number of outer spline ridges 265 adapted to interface with a scale drum. As appears, one of the splines is different allowing it to rotationally mate with a corresponding scale drum spline.

Figure 6:
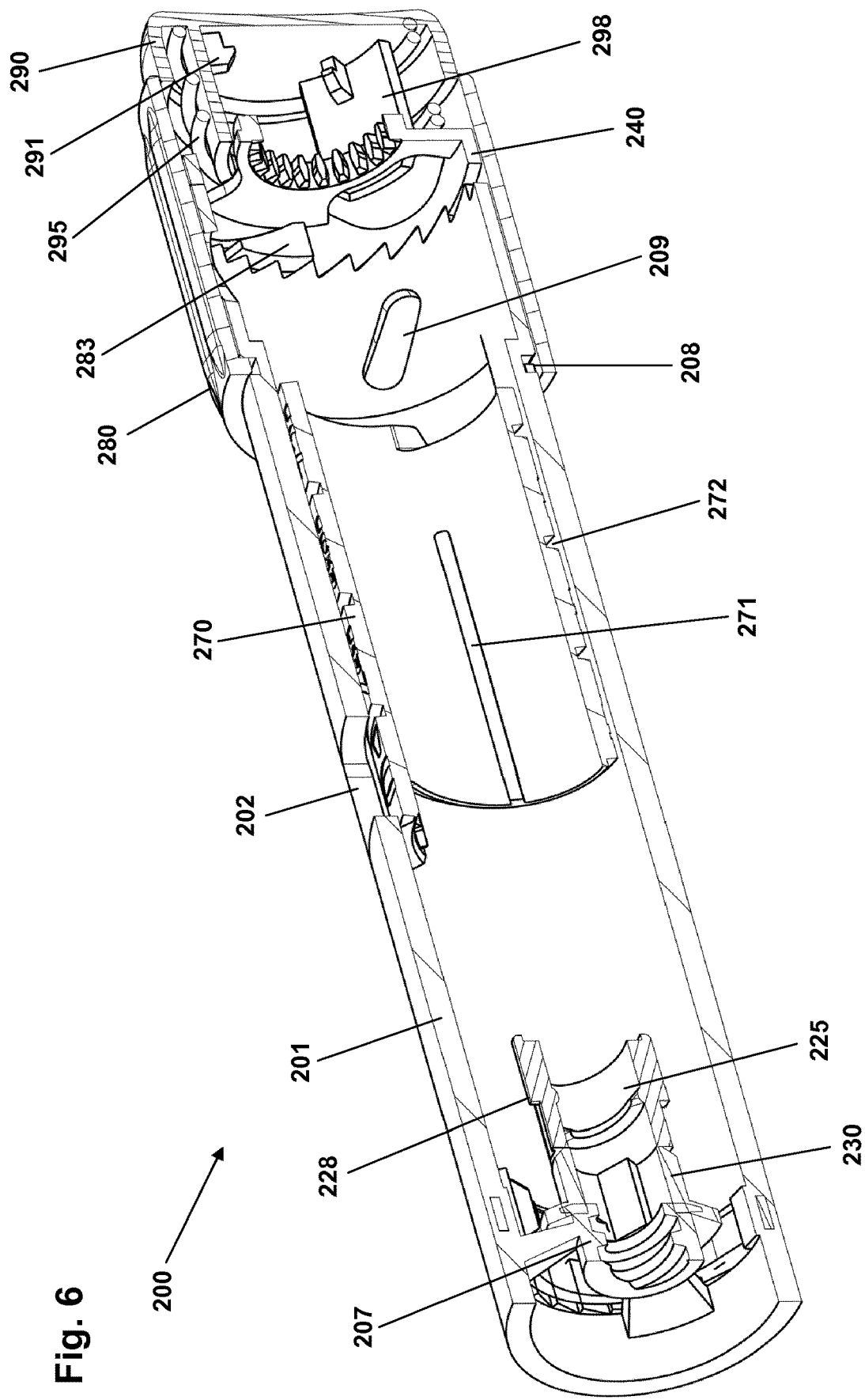
FIG. 6 shows in cross-section the proximal portion of the first embodiment in a partly assembled state.

Turning to FIG. 6 the housing member proximal portion, the dose setting member, the transmission member and the release button are shown in an assembled state. The figure further shows the scale drum 270 provided with an inner longitudinal spline 271 for engagement with the drive tube and an outer helical groove 272 for threaded connection with the housing inner surface. To allow the ratchet interface to be visible, the drive tube and the torsion spring have been omitted in FIG. 6.

More specifically, the dose setting member 280 is mounted rotationally free but axially locked on the housing member by means of the flanges arranged in the circumferential housing groove 208. The transmission member 240 is mounted non-rotationally on the drive tube (see FIG. 7) by means of a splined connection allowing the transmission member to move axially relative to both the drive tube and the dose setting member. Further, the release button 290 is mounted rotationally free but axially locked to the proximal end of the drive tube by means of a number of snap members 291 engaging the drive tube proximal flange 261. The release button further comprises a number of leg portions 298 adapted to be moved through the transmission member openings 248. A bias means in form of a return spring 295 is arranged between the transmission member 240 and the release button, the return spring urging the transmission member ratchet teeth 243 into engagement with the housing member ratchet teeth 203 as shown. As can also be seen in FIG. 6 one of the drive-lift ratchet control structures 283 is arranged corresponding to a transmission member drive section, the two drive surfaces and the two lift surfaces engaging each other. As appears, in the engaged position the ratchet prevents the transmission member, and thus the drive tube, from being turned counter-clockwise.

When setting a dose the dose setting member is rotated clockwise. As the drive surfaces 287 of the drive-lift ratchet control structures 283 are in engagement with the corresponding drive surfaces 247 on the transmission member the latter is forced to rotate together with the dose setting member to the desired rotational position, this resulting in the transmission member ratchet teeth passing over the housing ratchet teeth during which the transmission member is moved back and forth due to the inclined ratchet teeth, the return spring and the splined connection with the drive tube. The dose can be set in increments corresponding to one ratchet tooth which e.g. for a given insulin delivery device typically will correspond to one unit (IU) of insulin formulation. During dose setting the drive spring is strained correspondingly. To ensure a proper drive torque also for smaller doses the drive spring is pre-strained in the initial state.

When decreasing a set dose the dose setting member is rotated counter-clockwise whereby a gap is created between the drive surfaces on the drive-lift ratchet control structure 283 respectively the transmission member. However, as the inclined lift surfaces 286 of the drive-lift control structures are in engagement with the corresponding lift surfaces 246 on the transmission member the latter is moved proximally against the return spring until the transmission member ratchet teeth just disengages the housing ratchet teeth, at which point the force from the strained spring will rotate the drive tube counter-clockwise and thereby also the transmission member, this resulting in the inclined lift surfaces disengaging each other. As a consequence the transmission member can be moved distally by the return spring whereby the ratchet teeth will re-engage, this corresponding to the previously set dose having been decreased by one increment. If the user continuous to rotate the dose setting member counter-clockwise the set dose will continue to be reduced by one increment for each back and forth movement of the transmission member. At the same time the scale drum is also rotated counter-clockwise and the dose size shown in the display window 202 is reduced correspondingly.

Figure 7:
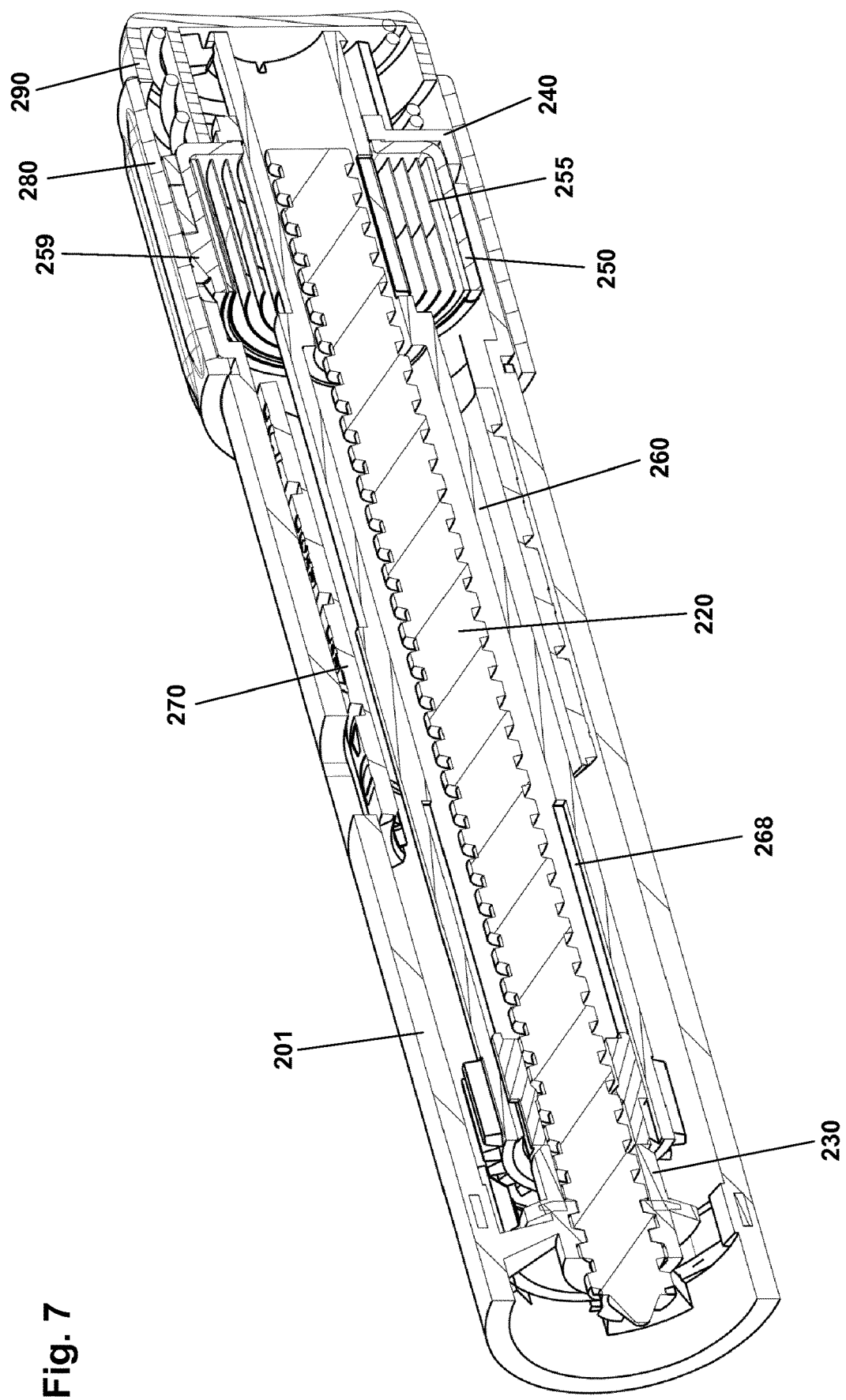
FIG. 7 shows in cross-section the proximal portion of the first embodiment in an assembled state.

Turning to FIG. 7 the figure shows the device of FIG. 6 with further components of the dose setting and expelling mechanism arranged inside the housing 201. More specifically, the figure shows a drive tube 260 in splined connection with the scale drum 270, a non-helical clock-type torsion drive spring 255 mounted in a cup-shaped spring housing 250 and connected to the spring housing respectively the drive tube, a threaded piston rod 220 arranged inside the drive tube and being threadedly connected to a stationary housing nut portion 207, a piston driver 230 arranged non-rotatable but axially moveable on the piston rod, as well as a drive coupling 263 allowing the drive tube to be coupled in and out of engagement with the piston driver. The spring housing comprises a number of oblong lateral projections 259 adapted to be slidingly received in the inclined housing slots 209, this allowing the spring housing and spring to be moved axially back and forth as the drive tube is moved back and forth during actuation, the inclined slots together with the spring torque ensuring that the spring housing and associated structures will be moved proximally when the device is not actuated. The spring housing is described in greater detail in EP 15165735.0. The device further comprises an end-of-content member 225 in threaded engagement with the piston rod and in splined engagement with the drive tube via splines 228 received in corresponding axial grooves 268. To expel a set dose of drug the actuation button 290 is moved distally against the axial forces of the return spring and the drive spring whereby firstly the distal end of the drive tube 260 engages the piston driver 230 via the drive coupling 263 and secondly the drive tube splines of the release coupling disengages the transmission member splines 242, this allowing the strained spring 255 to rotate the drive tube and thereto coupled piston driver and piston rod 220 counter-clockwise, this resulting in the piston rod being moved distally through the threaded housing nut 207. When the user releases the pressure on the actuation button the return spring and the drive spring serve to return the button and drive tube in the proximal direction and thereby firstly re-engage the splined connection between the drive tube and the transmission member and secondly dis-engage the drive tube from the piston driver, this movement also allowing a partly expelled dose to be paused.

As appears, the drive mechanism disclosed in FIGS. 6 and 7 comprises a drive spring 255 and a scale drum 270 which both are arranged in the circumferential space between the drive tube 260 and the housing 201 but axially apart. Further, as the drive coupling is located at the distal end of the drive tube this allows the proximal portion of the piston rod 220 to be housed in the drive tube without additional components arranged between the piston rod and the drive tube inner surface, this providing a design with a smaller number of "layers" and thus a smaller diameter as would otherwise be the case.

Figure 8:
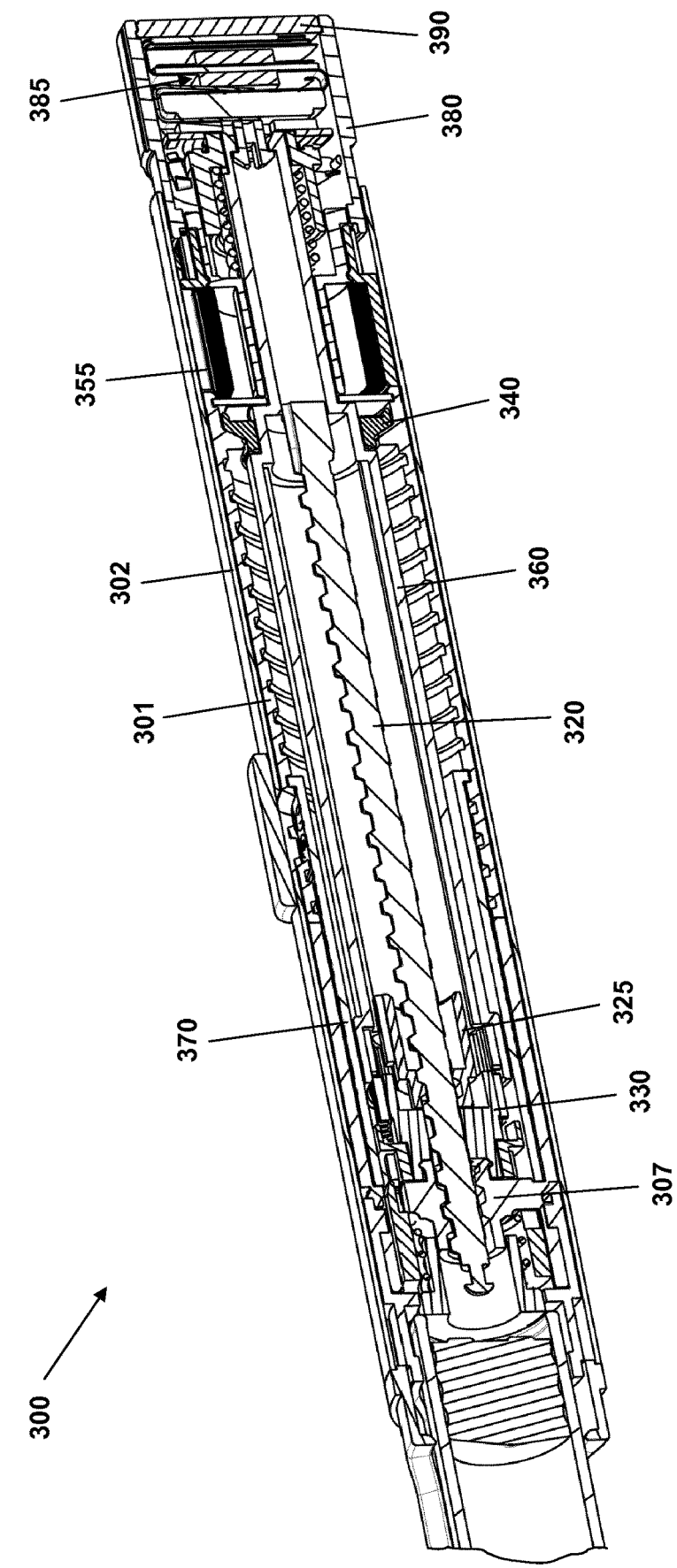
FIG. 8 shows in cross-section the proximal portion of a second embodiment of a drug delivery device.

With reference to FIG. 8 a second exemplary embodiment 300 incorporating aspects of the present invention, a compact expelling mechanism for a drug delivery device, will be described. The mechanism is similar to the mechanism described above with reference to FIGS. 2-7 and basically comprises a number of inner housing portions 301 arranged inside a common tubular sleeve 302 to provide a combined housing, a housing nut portion 307, a drive tube 360, a torsion drive spring 355 arranged between a housing portion and the drive tube, a scale drum 370 also arranged between a housing portion and the drive tube, a transmission member 340, a piston rod 320, a piston driver 330, and an end-of-content member 325.

The scale drum 370 is arranged in the circumferential space between the drive tube 360 and the housing member 301, the scale drum being rotationally locked to the drive tube via longitudinal splines (not seen) and being in rotational threaded engagement with an inner helical thread 303 of the housing member via cooperating thread structures 373, whereby the helical row of numerals passes the display window opening 304 in the housing member when the drum is rotated relative to the housing by the drive tube.

The spline connection comprises a number of ridge/tooth structures, typically two or three, in sliding engagement with corresponding grooves. The grooves may be formed in the scale drum inner surface and the ridge structures being formed on the drive tube outer surface, the ridge structures thereby having an axial position which does not move during dose setting. Alternatively, the grooves may be formed in the drive tube outer surface and the ridge structure being formed on the scale drum inner surface, the ridge structures thereby having an axial position which move axially during dose setting. For such spline connections the proximal-most of the ridge structures could be said to define the proximal-most axial position of the spline connection. This said, in most spline connections the ridge structures are arranged at the same axial position just as ridge structures are arranged on either of the two splined members. In the shown embodiment the housing helical thread is arranged proximally of the display window 304. Depending on the orientation of the helical thread the scale drum may move proximally from an initial distal position during dose setting, or it may move distally from an initial proximal position during dose setting.

The dose setting member is in the form of a combined dose setting and release member 380. In contrast to the first embodiment a moveable spring housing is not provided, but the combined dose setting and release member 380 houses a dose logging unit 385 comprising electronic circuitry, a rotational sensor and a display, the logging unit being adapted to detect the size of set and/or expelled dose amounts. The display is covered by a proximal window 390 serving as a button surface for releasing the expelling mechanism. As the logging unit is not part of the present invention it will not be described in greater detail.

The transmission member 340 is located distally of the drive spring and as in the first embodiment it interacts with the housing to provide a two-way dose setting ratchet mechanism and the drive tube to provide a release coupling. The scale drum 370, the drive member 330, the drive coupling and the end-of-content member 325 are arranged similar to the first embodiment and generally works in the same way.

The operation and working principles of the second embodiment are generally identical to the first embodiment, i.e. the user sets a dose to be expelled and strains the drive spring by rotating the a combined dose setting and release member 380, the drive tube and drive spring being held in their set rotational position by means of the release coupling. Subsequently the user moves the combined dose setting and release member 380 distally, this resulting in the drive coupling being activated and the release coupling subsequently released whereby the set dose of drug is expelled.

As appears, the drive mechanism disclosed in FIG. 8 comprises a drive spring 355 and a scale drum 370 which both are arranged in the circumferential space between the drive tube 360 and the housing 301, 302 but axially apart and thus non-overlapping with the scale drum in its proximal-most position.

Further, as the drive coupling is located at the distal end of the drive tube this allows the proximal portion of the piston rod 320 to be housed in the drive tube without additional components arranged there between, this providing a design with a smaller number of "layers" and thus a smaller diameter as would otherwise be the case.

Figure 9:
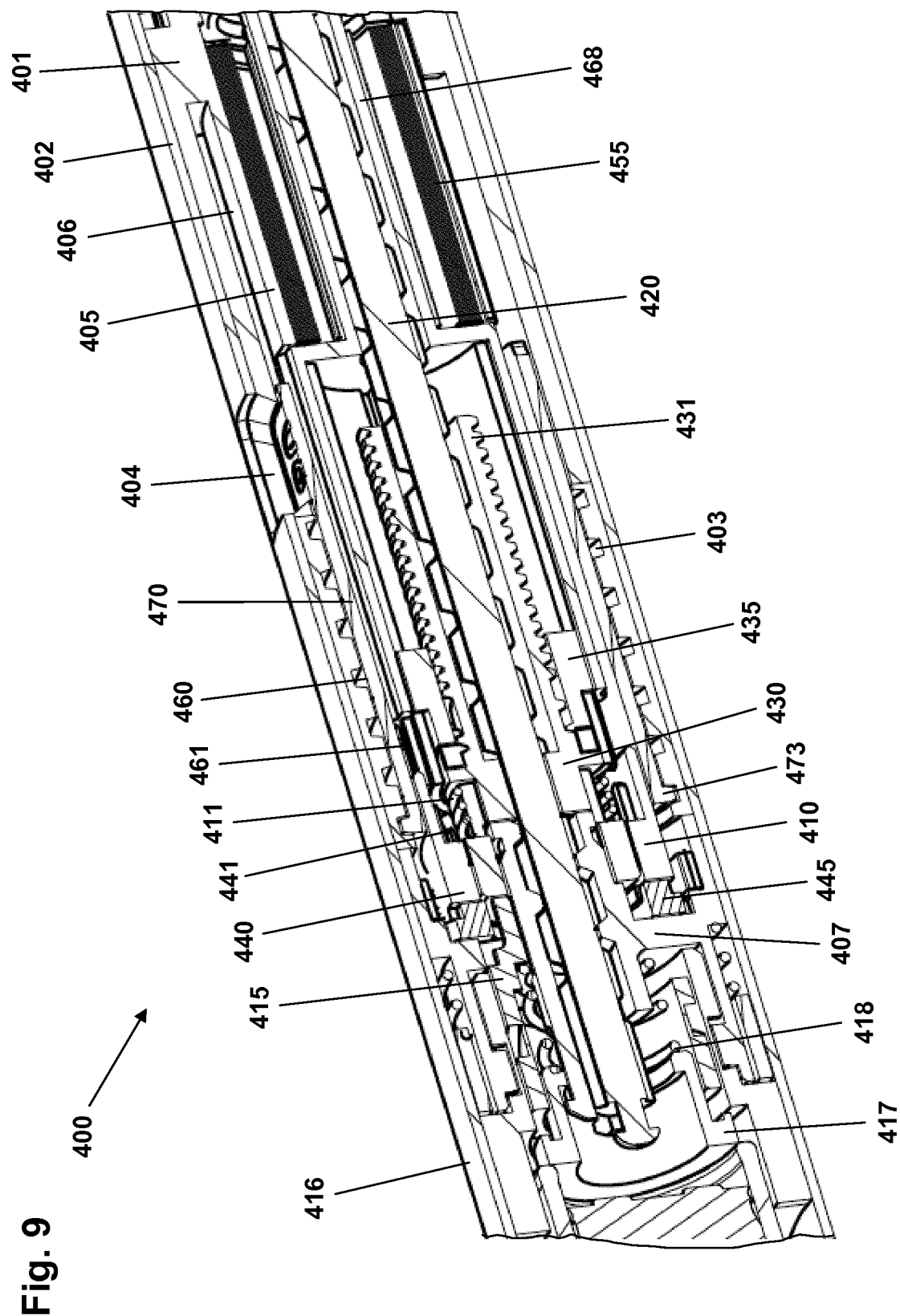
FIG. 9 shows in cross-section a portion of a third embodiment of a drug delivery device.

With reference to FIG. 9 a third exemplary embodiment incorporating aspects of the present invention, a compact expelling mechanism for a drug delivery device, will be described. The proximal not shown portion of the mechanism is similar to the mechanism described above with reference to FIG. 8, however, the distal portion of the mechanism comprising the drive coupling has been modified.

More specifically, the drug delivery device 400 comprises a number of inner housing portions 401 arranged inside a common tubular sleeve 402 to provide a combined housing, a housing nut portion 407, a drive tube 460, a scale drum 470 arranged between a housing portion and the drive tube, a spiral drive spring 455, a threaded piston rod 420, a piston driver 430, a coupling member 410, a coupling member spring 411 and a ratchet member 440. The device further comprises a coupling actuator 415, a cartridge holder member 416, a cartridge support 417, a cartridge support spring 418, a brake member 445 and an end-of-content member 435. The inner housing comprises a tubular inner housing portion 405 serving as an anchor structure for the outer end of the drive spring, a circumferential space 406 being defined between the inner housing and the tubular inner housing portion.

The scale drum 470 is rotationally locked to the drive tube via longitudinal splines (not seen) and is in rotational threaded engagement with an inner helical thread 403 of the housing member via cooperating thread structures 473, whereby the helical row of numerals passes the display window opening 404 in the housing member when the drum is rotated relative to the housing by the drive tube. In the shown distal position the scale drum 470 is arranged in the circumferential space between the drive tube 460 and the housing member 401, whereas when it is moved proximally it is received in the circumferential housing space 406. The drive tube comprises a proximal narrow-diameter portion 468 adapted to receive the piston rod in its proximal position.

The drive spring 455 is arranged in the circumferential space between the drive tube narrow-diameter proximal portion 468 and the tubular inner housing portion 405. As appears, when the scale drum 470 is in its distal-most position it is arranged distally of the drive spring 455, whereas the scale drum moves into an overlapping state with the drive spring as it is moved proximally during dose setting.

The spline connection comprises a number of ridge/tooth structures, typically two or three, in sliding engagement with corresponding grooves. The grooves may be formed in the scale drum inner surface and the ridge structures being formed on the drive tube outer surface, the ridge structures thereby having an axial position which does not move during dose setting. Alternatively, the grooves may be formed in the drive tube outer surface and the ridge structure being formed on the scale drum inner surface, the ridge structures thereby having an axial position which move axially during dose setting. For such spline connections the proximal-most of the ridge structures could be said to define the proximal-most axial position of the spline connection. This said, in most spline connections the ridge structures are arranged at the same axial position just as ridge structures are arranged on either of the two splined members. In the shown embodiment the housing helical thread 403 is arranged distally of the display window 404. Depending on the orientation of the helical thread the scale drum may move proximally from an initial distal position during dose setting, or it may move distally from an initial proximal position during dose setting. In the shown embodiment the scale drum 470 moves proximally from an initial distal position during dose setting The piston driver 430 is arranged non-rotatable but axially moveable on the piston rod. The piston driver 430 comprises a proximal tubular extension 431 on which the end-of-content member 435 is arranged in threaded engagement, the end-of-content member further being coupled to the drive tube 460 by splines, this providing that the end-of-content member is moved proximally during dose setting. The ratchet member 440 is coupled to the housing and allowed to rotate uni-directionally during out-dosing. The coupling member 410 is in splined connection with both the drive member 430 and the ratchet member 440, this providing that the drive member 430 is rotationally locked to the housing during dose setting. The ratchet member 440 is provided with inner proximal splines 441 adapted to receive drive tube distal outer splines 461, this providing an actuatable drive coupling. The ring-shaped brake member 445 is arranged between the housing and ratchet member 440. The working principle of the brake member is described in detail in WO 2015/055642.

The cartridge support spring 418 is arranged between the cartridge support 417 and the coupling actuator 415 and exerts a distally directed biasing force on the cartridge support 417. The coupling member spring 411 is arranged between the coupling member 410 and the drive member 430 and exerts a distally directed biasing force on the coupling member 410.

To expel a set dose of drug the actuation button is moved distally against the axial forces of the return spring (as in the FIG. 8 embodiment) whereby firstly the distal spline end 461 of the drive tube 460 engages the ratchet member proximal splines 441 and thereby, via the coupling member 410, the piston driver 430, and secondly the drive tube release coupling disengages (as in the FIG. 8 embodiment), this allowing the strained spring to rotate the drive tube and thereto coupled piston driver and piston rod 420, this resulting in the piston rod being moved distally through the threaded housing nut 407. When the user releases the pressure on the actuation button the return spring serve to return the button and drive tube in the proximal direction and thereby firstly re-engage the proximal release coupling and secondly dis-engage the drive tube 440 from the ratchet member 460 and thereby from the piston driver 430, this movement also allowing a partly expelled dose to be paused.

Although not shown in FIG. 9, the third embodiment is provided with a front-loaded cartridge holder comprising the shown rotatable cartridge holder member 416 which is coupled to the coupling actuator. When the cartridge holder member 416 is rotated to open the distal cartridge-receiving end of the cartridge holder, the coupling actuator 415 is moved proximally whereby the coupling member 410 against the bias of the coupling member spring 411 is moved out of its splined engagement with the ratchet member 440, this allowing the coupling member, the drive member 430 and thereby the piston rod 420 to rotate, whereby the piston rod can be rotated proximally through the threaded nut portion 407, this allowing a new cartridge to be inserted in the cartridge holder. When the cartridge holder member 416 is rotated in the opposite direction to close the cartridge holder, the coupling actuator 415 is moved distally, this allowing the coupling member 410 to re-engage the ratchet member 440, the coupling member being biased distally by the coupling member spring 411.

In an alternative embodiment (not shown) the drug delivery device described with reference to FIG. 9 may be provided with a traditional rear-loaded cartridge holder, the coupling actuator 415 being actuated when the cartridge holder is de-coupled from the drive assembly portion.

With reference to FIGS. 10-15 an exemplary embodiment of a further ratchet mechanism which may be used in the context of the present invention will be described. It should be noted that the drive spring is not arranged corresponding to the above-described embodiment. The mechanism basically comprises a housing member 501, a drive tube 560, a helical torsion spring 555 arranged between the housing and the drive tube, a transmission member 540, a drive-lift control member 590, a combined dose setting and release member 580 and a return spring 595. The main difference between the first and second embodiment is that the functionality of the dose setting member has been split into two members, this allowing the dose setting member to move axially relative to the housing. Otherwise the general working principles of the two embodiments are the same as will be apparent from the detailed description of the working principle given below, however, first some of the central components of the dose setting mechanism will be described in detail.

Figure 10:
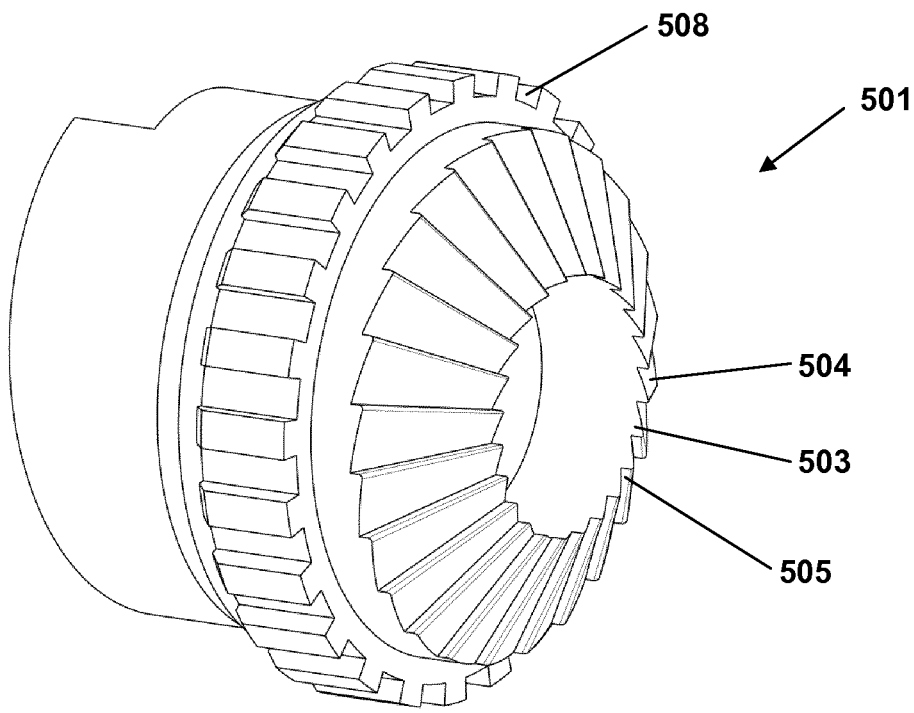
FIG. 10 shows a ratchet part of a further embodiment of an alternative ratchet mechanism.

Turning to FIG. 10 a housing base member 501 defining a longitudinal reference axis is shown. The housing base member is attached to the proximal end of a tubular main housing member 509 (see FIG. 14) and forms the base for a drive spring. The housing member comprises a proximally-facing conical surface on which a plurality of ratchet teeth structures 503 (here: 24) is arranged around a central opening, each tooth having a triangular configuration with an inclined ratchet surface 504 and a stop surface 505 oriented perpendicularly to the housing member cross-sectional plane. The housing base member further comprises an outer circumferential array of longitudinal splines 508 adapted to engage the dose setting member. In this way a first ratchet part coupled non-rotationally to the housing and comprising a plurality of ratchet teeth is formed. As appears, in this embodiment the first ratchet part is formed integrally with the housing base member.

Figure 11:
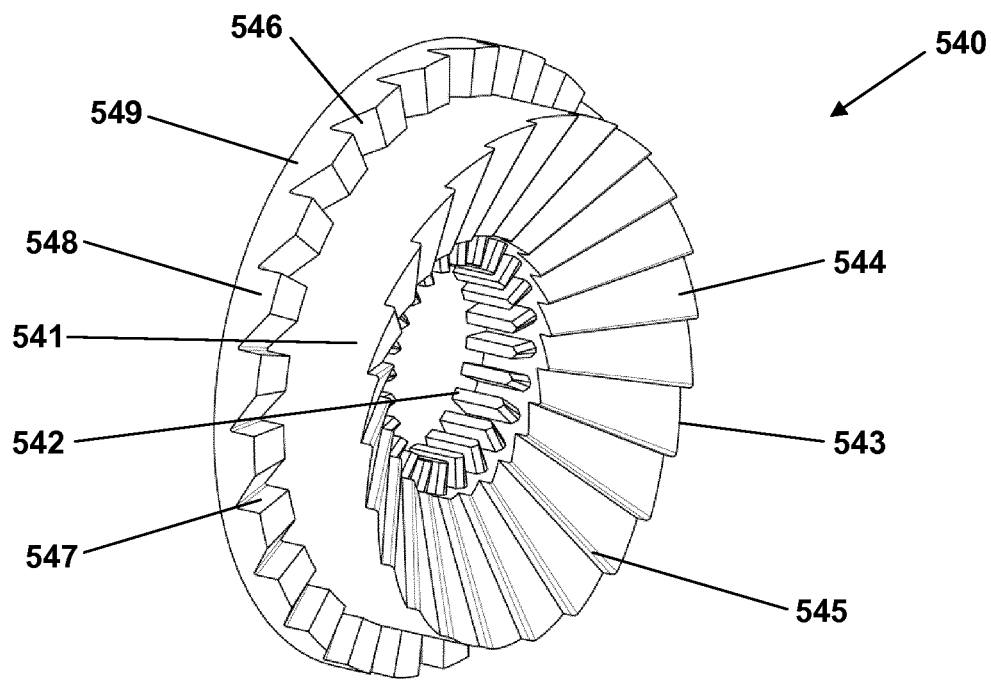
FIG. 11 shows a further ratchet part of the alternative ratchet mechanism.

FIG. 11 shows the transmission member 540 having a ring-shaped body portion 541 with a central opening provided with a plurality of longitudinally arranged splines 542 adapted to slidingly engage corresponding spline grooves on the drive tube. The transmission member comprises a distally-facing (when mounted) concave surface on which a first plurality of ratchet teeth structures 543 (here: 24) is arranged around the central opening, each tooth having a triangular configuration with an inclined ratchet surface 544 and a stop surface 545 oriented perpendicularly to the housing member cross-sectional plane, the ratchet teeth being configured to interface with the corresponding ratchet teeth on the housing member to thereby provide a one-way ratchet. In this way a second ratchet part is formed. The transmission member further comprises an outer circumferential flange 549 with a second plurality (here: 24) of distally-facing (when mounted) ratchet teeth structures 548, each tooth having a configuration with an inclined lift surface 546 and a drive surface 547 oriented perpendicularly to the housing member cross-sectional plane. In the shown embodiment each tooth has a flat top. As appears, compared to the first embodiment the drive-lift surfaces have been separated from the main ratchet structure.

Figure 12:
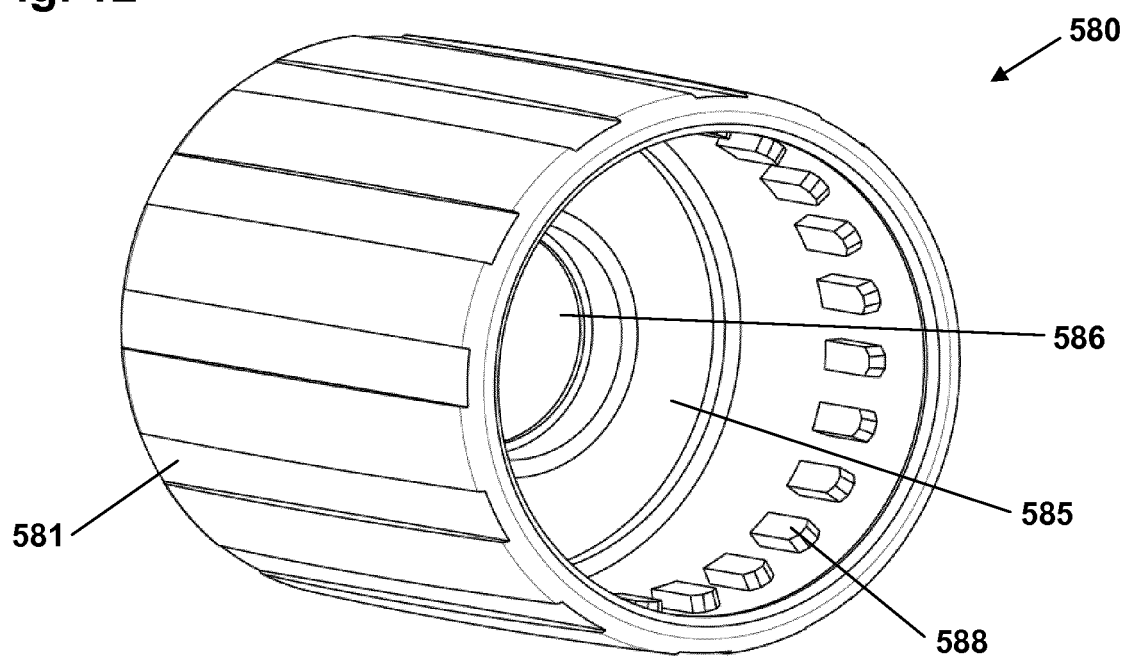
FIG. 12 shows a dose setting member of the alternative ratchet mechanism.

FIG. 12 shows the dose setting member 580 having a generally tubular configuration with an outer cylindrical surface with a plurality of longitudinally arranged ridges 581 providing a gripping surface, and an inner cylindrical surface comprising at the distal end a number of longitudinally arranged splines 588 adapted to interface with the housing member splines 508. The dose setting member further comprises an inner ring-formed transversal partition wall 585 with a central opening 586 adapted to rotationally interface with the drive tube proximal end.

Figure 13:
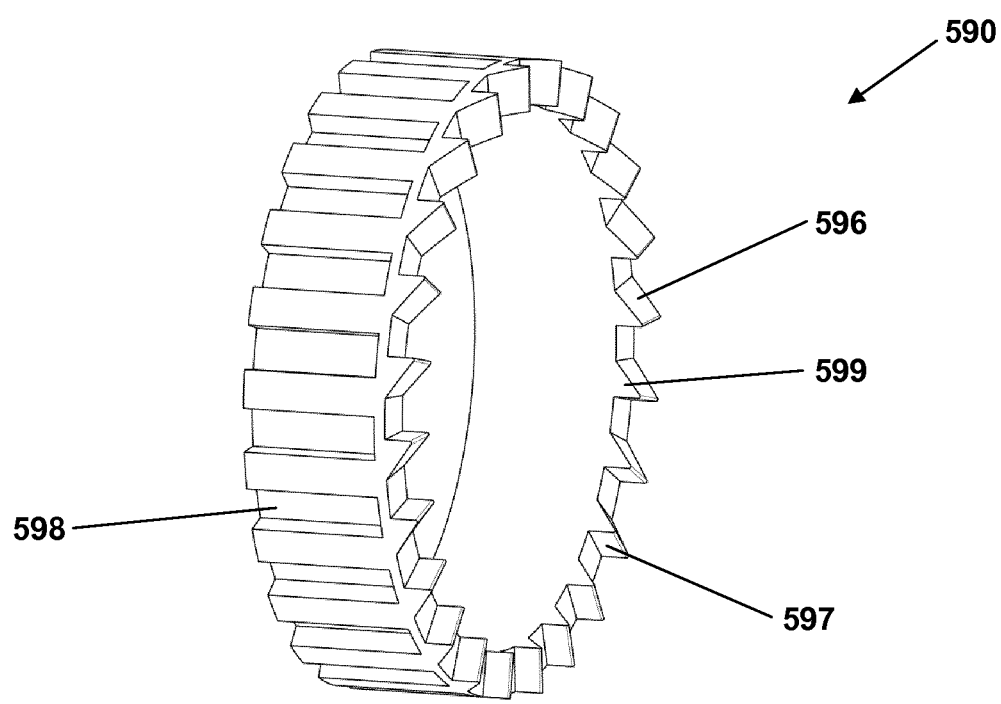
FIG. 13 shows a yet further ratchet part of the alternative ratchet mechanism.

The integrated drive-lift control structures of the first embodiment dose setting member have been transferred to a separate drive-lift control member. More specifically as shown in FIG. 13, the drive-lift member 590 is configured as a ring-formed member having an outer circumferential surface with a plurality of longitudinally arranged splines 598 adapted to interface with the dose setting member splines 588, as well as a plurality of proximally-facing drive-lift teeth 599 arranged on the proximal circumferential edge, each tooth having a triangular form with a longitudinally oriented drive surface 597 and an inclined lift surface 596 adapted to engage the corresponding drive-lift surfaces 547, 546 on the transmission member 540.

Figure 14:
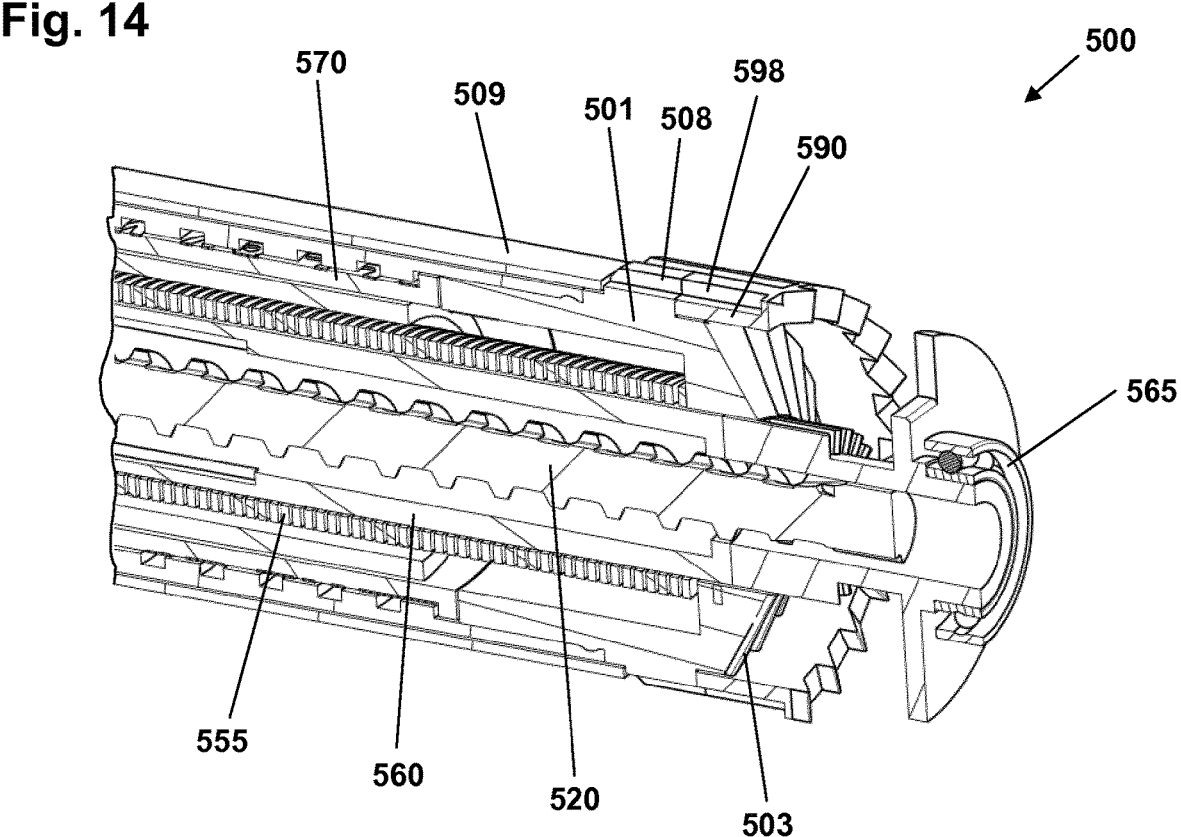
FIG. 14 shows in cross-section the alternative ratchet mechanism in a partly assembled state.
Figure 15:
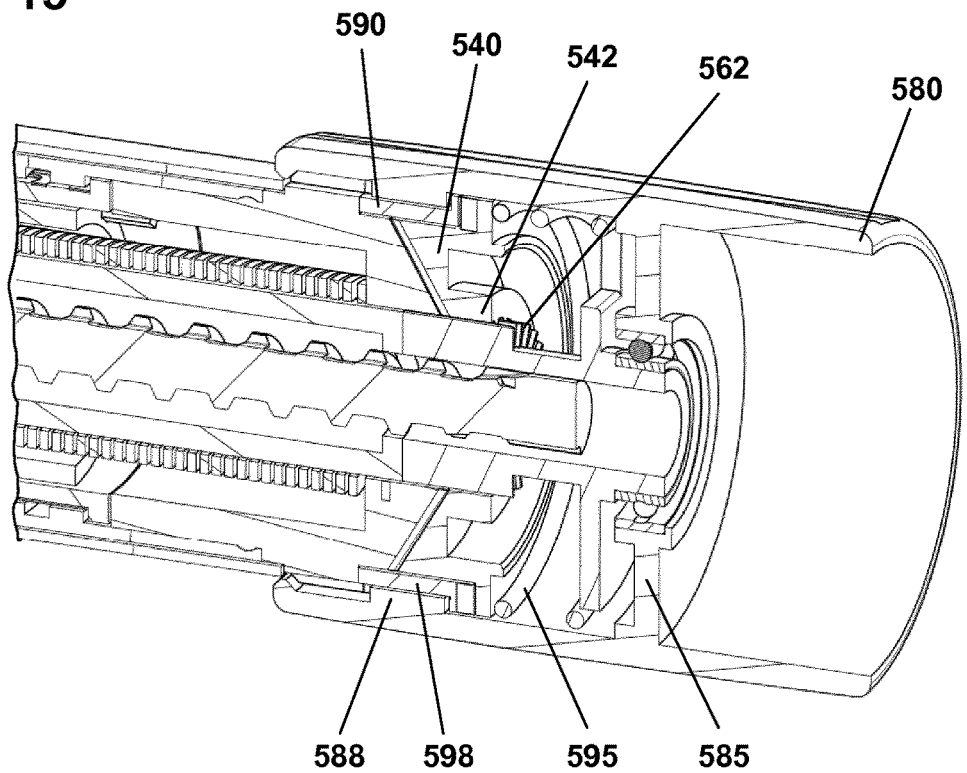
FIG. 15 shows in cross-section the alternative ratchet mechanism in an assembled state.

Turning to FIGS. 14 and 15 the proximal portion of a partly and fully assembled device 500 is shown. FIG. 14 shows a tubular main housing 509 to which the housing base member 501 is attached, the drive-lift control member 590, the drive tube 560 and a thereon mounted ball bearing 565, a helical drive spring 555 arranged around a portion of the drive tube and being connected to the spring base housing member 501 respectively the drive tube, a threaded piston rod 520 arranged inside the drive tube 560 and a scale drum 570 in threaded engagement with the housing main. In FIG. 15 further the transmission member 540, the dose setting member 580 and the return spring 595 have been mounted. Corresponding to the first embodiment the distal portion of the device comprises a piston drive member and a drive coupling arrangement (not shown).

More specifically, the dose setting member 580 is mounted axially moveable relative to the housing member 501 between a proximal position (as shown in FIG. 15) in which the splines 588 engages the splines 598 on the drive-lift control member 590, this allowing the dose setting member to rotate during dose setting, and a distal position in which the splines 588 engages the splines 508 on the housing member, this rotationally locking the dose setting member to the housing member. In the shown embodiment the dose setting member remains in splined connection with control member. Further, the dose setting member is mounted axially locked but rotationally free on the drive tube proximal end by means of a ball bearing 565, this allowing the dose setting member to serve as a combined dose setting and actuation member as will be described below. The proximal open end of the dose setting member is closed by a circular plate (not shown).

The transmission member 540 is mounted non-rotationally on the drive tube by means of a splined connection 542, 562 allowing the transmission member to move axially relative to both the drive tube and the dose setting member. A bias means in the form of a return spring 595 is arranged between the transmission member and the dose setting member partition wall 585, the return spring urging the transmission member ratchet teeth 543 into engagement with the housing member ratchet teeth 503 as shown. As appears, in the engaged position the ratchet prevents the transmission member, and thus the drive tube, from being turned counter-clockwise. As shown in FIG. 14 the drive-lift control member 590 is during dose setting rotationally locked to the dose setting member via the splined connection, and the drive-lift teeth of the drive-lift member and the transmission member are urged into engagement by the return spring.

When setting a dose the dose setting member in its proximal position is rotated clockwise. As the drive surfaces 597 of the drive-lift control member 590 are in engagement with the corresponding drive surfaces 547 on the transmission member 540 the latter is forced to rotate together with the dose setting member to the desired rotational position, this resulting in the transmission member ratchet teeth 543 passing over the housing member ratchet teeth 503 during which the transmission member is moved back and forth due to the inclined ratchet teeth, the return spring 595 and the splined connection with the drive tube. The dose can be set in increments corresponding to one ratchet tooth which e.g. for a given insulin delivery device typically will correspond to one unit (IU) of insulin formulation.

When decreasing a set dose the dose setting member is rotated counter-clockwise whereby a gap is created between the drive surfaces on the drive-lift control member 590 respectively the transmission member 540. However, as the inclined lift surfaces 596 of the drive-lift control member are in engagement with the corresponding lift surfaces 546 on the transmission member the latter is moved proximally against the return spring until the transmission member ratchet teeth just disengages the housing member ratchet teeth, at which point the force from the strained drive spring 555 will rotate the drive tube counter-clockwise and thereby also the transmission member, this resulting in the inclined lift surfaces disengaging each other. As a consequence the transmission member can be moved distally by the return spring whereby the ratchet teeth will re-engage, this corresponding to the previously set dose having been decreased by one increment. If the user continuous to rotate the dose setting member counter-clockwise the set dose will continue to be reduced by one increment for each back and forth movement of the transmission member. At the same time the scale drum is also rotated counter-clockwise and the dose size shown in the display window is reduced correspondingly.

To expel a set dose of drug the combined dose setting and actuation member 580 is moved distally against the force of the return spring 595 whereby at first the dose setting member connects to the splines 508 of the housing spring base member 501 to prevent further adjustment of the set dose, secondly the distal end of the drive tube 560 engages the piston driver via the drive coupling, and thirdly the drive tube splines disengages the transmission member splines 542, this allowing the strained spring 555 to rotate the drive tube and thereto coupled piston driver and piston rod 520 counter-clockwise, this resulting in the piston rod being moved distally through a threaded housing nut. When the user releases the pressure on the combined dose setting and actuation member the return spring serves to return the member and drive tube in the proximal direction and thereby firstly re-engage the splined connection between the drive tube and the transmission member and secondly dis-engage the drive tube from the piston driver, this movement also allowing a partly expelled dose to be paused.

The drive-lift teeth structures on the ratchet member 540 respectively the control member 590 may be configured corresponding to two alternatives, either with "non-inclined" drive surfaces corresponding to the embodiments described with reference to FIGS. 10-15 or, alternatively, with "inclined" drive surfaces to provide an over-torque protection mechanism during dial-up, this as described in greater in EP16186501.9.

Figure 16:
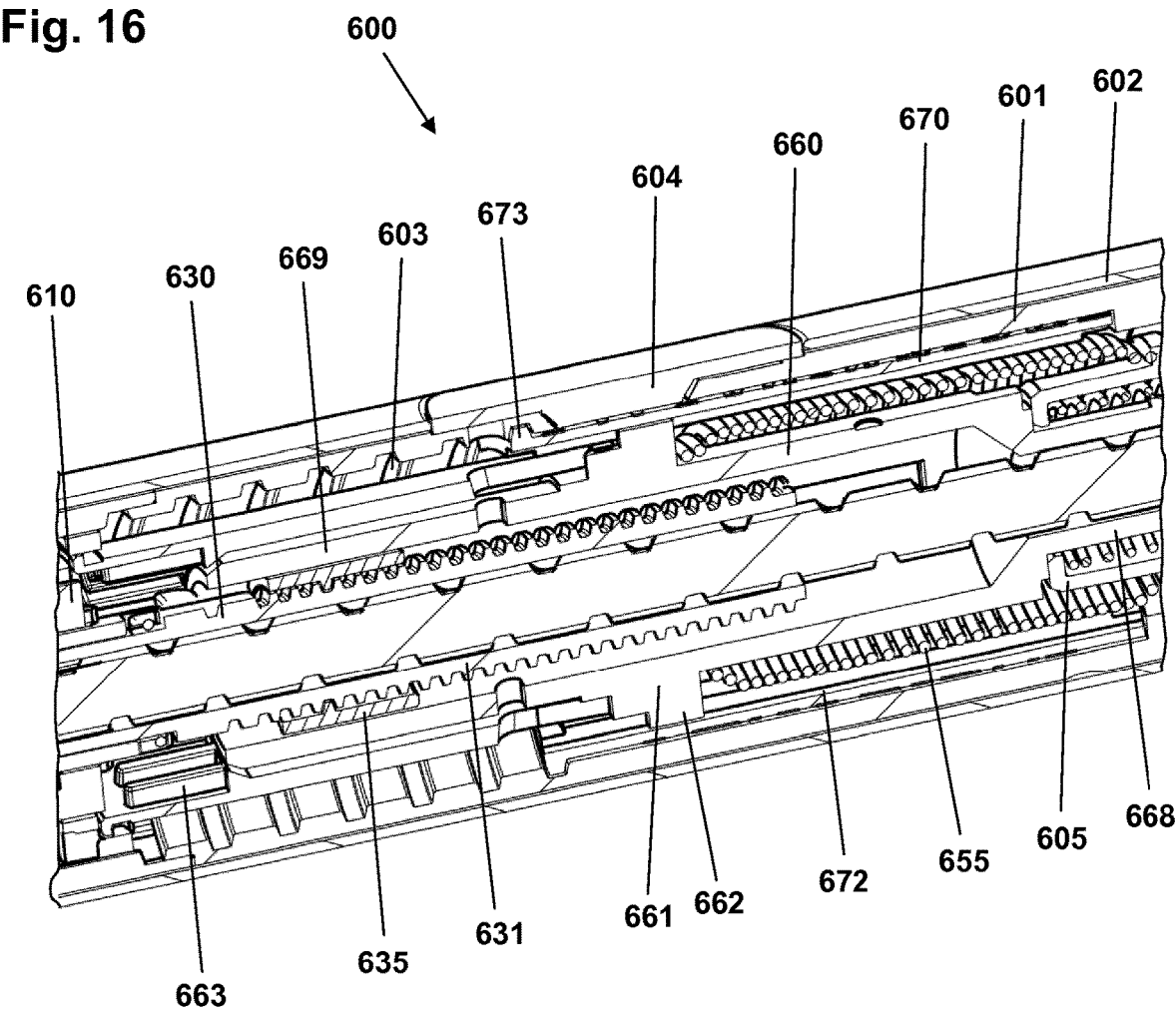
FIG. 16 shows in cross-section the central portion of a further embodiment of a drug delivery device.

With reference to FIG. 16 a further exemplary embodiment incorporating aspects of the present invention, a compact expelling mechanism for a drug delivery device, will be described. More specifically, FIG. 16 shows the central portion of a drive mechanism embodying a compact arrangement of a housing member, a drive tube, a drive member, a piston rod and a drive spring. The figure does not show the distal and proximal portions of the drug delivery device as these are not considered relevant for the described aspect of the invention.

More specifically, the drug delivery device 600 comprises an inner housing 601 arranged inside a tubular sleeve 602 to provide a combined housing, a drive tube 660, a scale drum 670 arranged between a housing portion and the drive tube, a drive spring 655, a threaded piston rod 620, a driver 630 and a coupling member 610. The inner housing comprises a tubular inner housing portion 605 serving as a proximal stop for the drive tube as well as an anchor structure for the proximal end of the drive spring.

The scale drum 670 is arranged in the circumferential space between the drive tube 660 and the housing member 601, the scale drum being rotationally locked to the drive tube via longitudinal splines 662, 672 and being in rotational threaded engagement with an inner helical thread 603 of the housing member via cooperating thread structures 673, whereby the helical row of numerals passes the display window opening 604 in the housing member when the drum is rotated relative to the housing by the drive tube.

The drive tube is functionally a single member, however, in the shown embodiment it comprises for manufacturing purposes a longer inner tubular member 660 and a shorter outer tubular skirt member 669 coupled to each other to provide a rotationally and axially locked connection. The skirt member 669 comprises at the distal end an inner array of axially oriented distally facing splines 663 adapted to engage corresponding spline structures on the coupling member 610 in the expelling state. The drive tube comprises approximately in the middle a central circumferential flange 661. The drive tube comprises a proximal narrow-diameter portion 668 adapted to receive the piston rod in its proximal position.

The spline connection comprises a number of ridge/tooth structures (here: two) in sliding engagement with corresponding grooves. In the shown embodiment the grooves 672 are formed in the scale drum inner surface and the ridge structures 662 being formed on the drive tube outer surface, the ridge structures thereby having an axial position which does not move during dose setting. For such a spline connection the proximal-most of the ridge structures could be said to define the proximal-most axial position of the spline connection, however, in the shown embodiment the ridge structures are arranged at the same axial position. In the shown embodiment the housing helical thread 603 is arranged distally of the display window 604. Depending on the orientation of the helical thread the scale drum may move proximally from an initial distal position during dose setting, or it may move distally from an initial proximal position during dose setting. In the shown embodiment the scale drum is position in an initial proximal position.

The drive spring 655 is in the form of a helical open wound torsion spring with a distal hook portion for attachment to the drive tube corresponding to the central flange 661 and a proximal hook portion for attachment to the housing member corresponding to the inner tubular portion 605. In an assembled state the drive spring is pre-wound to provide a desirable initial torque. As appears, the drive spring is arranged just proximally of the spline ridge structures. With the scale drum 670 in the proximal-most position the drive spring is housed in the circumferential space between the drive tube 660 and the scale drum 670 whereas with the scale drum in its distal-most position the drive spring faces the inner housing.

Corresponding to the embodiment of FIG. 9 the driver 630 is in engagement with the piston rod 620 via a pair of opposed splines, the piston rod and the driver thereby rotating together when the driver via the coupling member 610 is rotated by the drive tube during dose expelling. The driver 630 comprises a proximal tubular extension 631 on which the end-of-content member 635 is arranged in threaded engagement, the end-of-content member further being coupled to the drive tube 660 by splines, this providing that the end-of-content member is moved proximally during dose setting.

In the above description of exemplary embodiments, the different structures and means providing the described functionality for the different components have been described to a degree to which the concept of the present invention will be apparent to the skilled reader. The detailed construction and specification for the different components are considered the object of a normal design procedure performed by the skilled person along the lines set out in the present specification. For example, a traditional helical torsion drive spring may be used.

The invention claimed is:

1. A drug delivery device comprising or adapted to receive a drug-filled cartridge, comprising:
a housing,
an expelling assembly comprising:
  a piston rod adapted to engage and axially displace a piston in a loaded cartridge in a distal direction to thereby expel a dose of drug from the cartridge, the piston rod having a proximal-most position,
  a drive tube at least partially accommodating the piston rod, the drive tube having an outer surface,
  a drive member arranged in engagement with the piston rod and adapted to rotate the piston rod,
  a helical drive spring arranged in engagement with the housing and the drive tube,
  a setting structure allowing a user to simultaneously set a dose amount to be expelled and strain the helical drive spring correspondingly by rotation of the drive tube, the setting structure comprising a rotatable dose setting member,
  a scale drum directly and helically coupled to the housing as well as axially moveable but non rotatably coupled in relation to the drive tube, the scale drum thereby being moved helically as the drive tube is rotated, and the scale drum having an outer surface and an inner surface,
  a coupling structure comprising a ratchet mechanism comprising a first ratchet part and a second ratchet part, actuatable between a dose setting state in which the drive tube can be rotated to a set position, and an expelling state in which the drive tube driven by the helical drive spring can rotate the drive member, and
  a release structure actuatable between a dose setting state and an expelling state to thereby actuate the coupling structure,
wherein the helical drive spring can be released to rotate the drive tube and thereby the drive member to thereby rotate and move the piston rod in the distal direction,
wherein the scale drum is coupled to the drive tube via a spline connection, the spline connection during dose setting having a proximal-most position corresponding to a proximal-most position of the scale drum,
wherein the helical drive spring is arranged proximally of the spline connection when the spline connection is in its proximal-most position,
wherein the helical drive spring with the scale drum in its proximal-most position being arranged at least partially between the scale drum and the drive tube,
  a control structure adapted to rotate the second ratchet part in a first direction to thereby set a dose when the dose setting member is rotated in a first direction, and move the first and the second ratchet parts axially out of engagement with each other when the dose setting member is rotated in a second direction,
  a drive-release ratchet having a plurality of ratchet drive surfaces and a plurality of ratchet release surfaces inclined relative to a rotational reference plane, and
  a control ratchet comprising a plurality of control drive surfaces and a plurality of control release surfaces inclined relative to the rotational reference plane,
wherein:
  the control drive surfaces are cooperating with the ratchet drive surfaces to rotate the second ratchet part in the first direction when the dose setting member is rotated in the first direction, and
  the control release surfaces are slidingly cooperating with the ratchet release surfaces to axially move the first and second ratchet parts axially out of engagement with each other when the dose setting member is rotated in the second direction,
  whereby, when the first and second ratchet parts have been axially dis-engaged, the helical drive spring will rotate the second ratchet part in the second direction to thereby reduce the set dose, the bias structure moving the first and second ratchet parts axially into engagement with each other again, this resulting in the set dose being reduced corresponding to one tooth of the ratchet mechanism.

2. The drug delivery device as in claim 1, wherein the spline connection comprises a proximal-most ridge structure in sliding engagement with a corresponding groove, the groove being formed in the scale drum inner surface and the proximal-most ridge structure being formed on the drive tube outer surface,
  whereby the proximal-most ridge structure, and thereby the spline connection, has an axial position which does not move during dose setting.

3. The drug delivery device as in claim 1, wherein the spline connection comprises a proximal-most ridge structure in sliding engagement with a corresponding groove, the groove being formed in the drive tube outer surface and the proximal-most ridge structure being formed on the scale drum inner surface,
  whereby the proximal-most ridge structure, and thereby the spline connection, has an axial position which moves during dose setting.

4. The drug delivery device as in claim 1, wherein the release structure comprises a release member axially moveable between a proximal dose setting position and an actuated distal dose expelling position.

5. The drug delivery device as in claim 1, wherein the setting structure comprises the rotatable dose setting member, and the coupling structure comprises:
  a first coupling arrangement actuatable between a dose setting state in which the setting member is rotationally locked to the drive tube and in which the drive tube can be held in a set position against a biasing force of the strained helical drive spring, and an expelling state in which the drive tube is rotationally de-coupled from the dose setting member and is allowed to be rotated by the helical drive spring, and
  a second coupling arrangement actuatable between a dose setting state in which the drive tube can rotate relative to the drive member and an expelling state in which the drive tube is rotationally locked to the drive member,
wherein the release structure, when actuated, actuates the first coupling arrangement from the dose setting state to the expelling state, and actuates the second coupling arrangement from the dose setting state to the expelling state.

6. The drug delivery device as in claim 5, wherein the release structure comprises a release member axially moveable between a proximal dose setting position and an actuated distal dose expelling position, and the dose setting member is coupled to and moves axially with the release member.

7. The drug delivery device as in claim 6, wherein the dose setting member and the release member is formed by a combined dose setting and release member or assembly.

8. The drug delivery device as in claim 1, wherein the ratchet mechanism allows the drive tube to be held in a set position against a biasing force of the strained helical drive spring.

9. The drug delivery device as in claim 8, wherein the setting structure comprises the rotatable dose setting member, and the coupling structure comprises:
   a first coupling arrangement actuatable between a dose setting state in which the setting member is rotationally locked to the drive tube and in which the drive tube can be held in the set position against the biasing force of the strained helical drive spring, and an expelling state in which the drive tube is rotationally de-coupled from the dose setting member and is allowed to be rotated by the helical drive spring, and
   a second coupling arrangement actuatable between a dose setting state in which the drive tube can rotate relative to the drive member and an expelling state in which the drive tube is rotationally locked to the drive member,
   wherein the release structure, when actuated, actuates the first coupling arrangement from the dose setting state to the expelling state, and actuates the second coupling arrangement from the dose setting state to the expelling state, and
   wherein the ratchet mechanism is in the form of a releasable one-way ratchet mechanism allowing a set dose to be reduced, the ratchet mechanism being associated with either the first or the second coupling arrangement.

10. The drug delivery device as in claim 9, wherein the ratchet mechanism comprises:
    the first ratchet part comprising a plurality of ratchet teeth, the first ratchet part being non-rotationally coupled to the housing during dose setting,
    the second ratchet part comprising a plurality of ratchet teeth adapted to rotationally engage the ratchet teeth on the first ratchet part, the second ratchet part being non-rotationally coupled to the drive member during dose setting, the first and the second ratchet parts being axially moveable relative to each other during dose setting,
    a bias structure for axially biasing the first and the second ratchet parts into engagement with each other.

11. The drug delivery device as in claim 1, wherein:
    the drive tube comprises a proximal portion and a distal portion, the proximal portion having a smaller diameter in relation to the distal portion, and
    the helical drive spring is arranged corresponding to the drive tube proximal portion.

12. The drug delivery device as in claim 11, wherein:
    the expelling assembly comprises an end-of-content member arranged in a circumferential space between the piston rod and the drive tube corresponding to the distal portion, the end-of-content member being axially moveable between a distal position and a proximal position relative to the piston rod.

* * * * *